United States Patent [19]

Kimura et al.

[11] Patent Number: 5,795,497
[45] Date of Patent: Aug. 18, 1998

[54] THIOURACIL DERIVATIVES AND METAL SURFACE-TREATING AGENT COMPRISING THEREOF

[75] Inventors: Mikio Kimura; Masayuki Aizawa. both of Tsukuba, Japan

[73] Assignee: Tokuyama Corporation, Yamaguchi-ken, Japan

[21] Appl. No.: 837,479

[22] Filed: Apr. 18, 1997

[51] Int. Cl.[6] .................... C09K 3/00; C09K 15/06; C07D 239/10
[52] U.S. Cl. .................... 252/182.18; 544/314
[58] Field of Search ............ 544/314; 252/182.18

[56] References Cited

U.S. PATENT DOCUMENTS

| | | | |
|---|---|---|---|
| 5,354,495 | 10/1994 | Urano et al. | 252/182.18 |
| 5,496,907 | 3/1996 | Dochniak | 528/73 |
| 5,563,214 | 10/1996 | Share et al. | 524/809 |

FOREIGN PATENT DOCUMENTS 2260984  5/1993  United Kingdom.

OTHER PUBLICATIONS

Chemical Abstracts, vol. 77, No. 22, 1972, Columbus, Ohio, US; abstract No. 100546r, p. 347; column 1; XP002042312, abstract.

Foye et al., "Metal–Binding Abilities of Antibacterial Heterocyclic Thiones", Journal of Pharmaceutical Sciences, vol. 61, No. 8, pp. 1209–1212, Aug. 1972.

Primary Examiner—Yogendra N. Gupta
Attorney, Agent, or Firm—Wenderoth, Lind & Ponack, L.L.P.

[57] ABSTRACT

A thiouracil derivative represented by the following general formula (1) or (2)

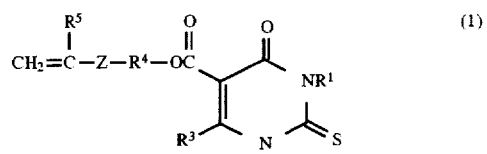

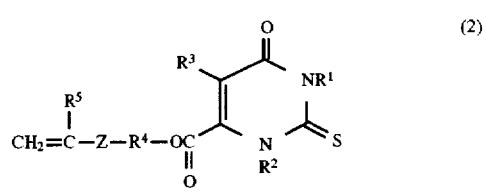

(wherein, $R^1$ and $R^2$ each are a hydrogen atom or an alkyl group, and at least one of $R^1$ and $R^2$ is a hydrogen atom, and $R^3$ is a hydrogen atom, an alkyl group or a phenyl group, and $R^4$ is a bivalent saturated hydrocarbon group having 2 to 12 carbon atoms, Z is —COO—, $CH_2O$— or —$C_6H_4$—$CH_2O$—, and $R^5$ is a hydrogen atom or a methyl group), and a metal surface-treating agent for bonding a metal, particularly a noble metal to a resin or the like in high adhesive strength and in high water resistance and high durability which contains the above thiouracil derivative and an organic solvent such as acetone or ethanol.

18 Claims, No Drawings

THIOURACIL DERIVATIVES AND METAL SURFACE-TREATING AGENT COMPRISING THEREOF

This invention relates to thiouracil derivatives each having a radical polymerizable unsaturated bond. These thiouracil derivatives can each be utilized, as a component for an adhesive for noble metals, in many fields such as medical treatment, electronic materials, precision instruments and jewelry wherein resins are bonded to metals, but are particularly useful in the dental field.

The invention further relates to a metal surface-treating agent containing such a thiouracil derivative, useful for exerting excellent adhesiveness to metals.

As adhesives for base metals such as iron, nickel, chromium, cobalt, tin, aluminum, copper and titanium, adhesives each containing an acrylic or methacrylic polymerizable monomer having a functional group such as a phthalic anhydride group, a phthalic acid group, a malonic acid group or a phosphoric acid group are proposed and put to practical use. However, an adhesive having sufficient adhesive strength to noble metals such as gold, platinum, palladium and silver has not been developed. Therefore, as to adhesion to noble metals, it has been common to plate the surface of such a noble metal with tin or oxidize the surface, in advance. Since these methods are complicated in operations and sufficient adhesive strength cannot be obtained thereby, the development of an adhesive for noble metals or a surface-treating agent for noble metals has been desired.

In order to meet the above requirement, adhesive polymerizable monomers each having a functional group such as a thiophosphoric acid group (Japanese Laid-open Patent Publication No. 138,282/1989), a thiophosphoryl chloride group (Japanese Laid-open Patent Publication No. 117,595/1993) or a triazinedithione derivative (Japanese Laid-open Patent Publication No. 83,254/1989) has been proposed in recent years. In surface-treating agents each containing such an adhesive polymerizable monomer, adhesion to a noble metal is made possible by previously applying such a surface-treating agent onto the surface of the noble metal, and then curing the polymerizable resin.

However, in the case of the adhesion of noble metals using the above surface-treating agents, there are problems that adhesive strength or water resistance, or durability is not yet sufficient, and moreover, since the adhesive polymerizable monomers are unstable, the storage stability of the surface-treating agents is poor, the adhesive strength is influenced by the application amount, and so on. Further, the effect of the above surface-treating agents is exerted only in the adhesion of noble metals, and not exerted in the adhesion of base metals. Thus, in this invention, it was aimed to provide a metal surface-treating agent which has sufficient initial adhesive strength to both base metals and noble metals, and is good in adhesion durability, water resistance and storage stability.

The present inventors had intensely studied for solving the above problems, and as a result, they found that thiouracil derivatives each having a radical polymerizable unsaturated bond and a surface-treating agent containing such a thiouracil derivative as a main component have effect on storage stability, adhesive strength to noble metals, water resistance, durability and so on, they further found that a surface-treating agent containing a thiouracil derivative having a radical polymerizable unsaturated bond and an acidic group-containing (meth)acrylate monomer has sufficient adhesive strength to both base metals and noble metals, and is excellent in storage stability, water resistance and durability, and they completed the invention.

Thus, the invention is a thiouracil derivative containing at least one radical polymerizable unsaturated bond in the molecule, a metal surface-treating agent containing the thiouracil derivative, a metal surface-treating agent containing a thiouracil derivative containing at least one radical polymerizable unsaturated bond in the molecule and an organic solvent, and a metal surface-treating agent containing the thiouracil derivative, an acidic group-containing (meth)acrylate monomer and an organic solvent.

The thiouracil derivative is not particularly limited so long as it contains a thiouracil group and at least one radical polymerizable unsaturated bond in the molecule, but it is preferably an unsaturated thiouracil derivative which has at at least one terminus thereof an organic group (I) having a radical polymerizable unsaturated bond, and has at the other terminus the following thiouracil residue (II)

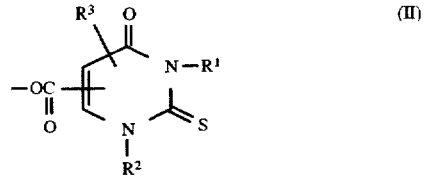

wherein $R^1$ and $R^2$ each are a hydrogen atom or an alkyl group, and at least one of $R^1$ and $R^2$ is a hydrogen atom, and $R^3$ is a hydrogen atom, an alkyl group or a phenyl group, and wherein the organic group (I) and the thiouracil residue (II) are separated by a bivalent spacer residue containing at least 2 carbon atoms.

In the above formula (II), $R^1$ and $R^2$ each represent a hydrogen atom or an alkyl group, and at least one of $R^1$ and $R^2$ is a hydrogen atom. As preferred alkyl groups, there can be exemplified alkyl groups having 1 to 4 carbon atoms such as a methyl group, an ethyl group, a propyl group and a butyl group.

Further in the above formula (II), $R^3$ represents a hydrogen atom, an alkyl group or a phenyl group. As the alkyl group, there can be exemplified the same alkyl groups as mentioned in the above $R^1$ and $R^2$.

A further preferred unsaturated thiouracil derivative is the above unsaturated thiouracil derivative wherein the organic group (I) having a radical polymerizable unsaturated bond is represented by the following formula (I-1)

wherein $R^5$ is a hydrogen atom or a methyl group, and Z is a —COO— group, a —CH$_2$O— group or a

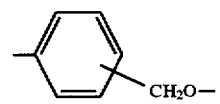

group, and the spacer residue is a bivalent organic group having 2 to 20 carbon atoms which may contain, in the chain skeleton, oxygen, or oxygen and silicon, besides carbon.

The spacer residue is not limited at all so long as it is a bivalent organic group having 2 to 20 carbon atoms which may contain, in the chain skeleton, oxygen, or oxygen and silicon, besides carbon. Therefore, the spacer residue includes not only a bivalent straight-chain or branched chain hydrocarbon group, but an organic group having an ether linkage, an ester linkage, a siloxane linkage or a phenylene group in the principal chain.

As specific examples of the spacer residue, there can be mentioned

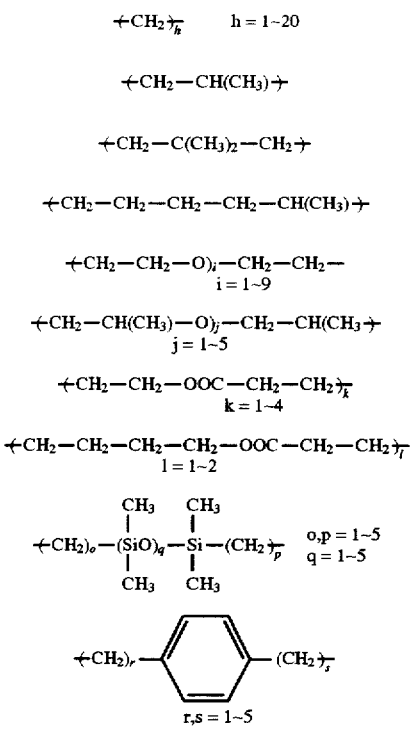

etc.

Preferred among the above spacer residues are bivalent saturated hydrocarbon groups each having 2 to 12 carbon atoms, and a group represented by the following formula (III-2), (III-3) or (III-4)

+CH₂CH₂O )ₙ CH₂CH₂  (III-2)

(III-3)

```
       CH₃   CH₃
        |     |
+CH₂)ₒ—(SiO)q—Si—(CH₂)ₚ
        |     |
       CH₃   CH₃
```

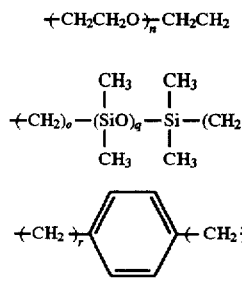  (III-4)

wherein n is an integer of 1 to 5, o and p each are an integer of 1 to 10, q is an integer of 1 to 5, and r and s each are an integer of 1 to 5.

When the spacer residue is a bivalent saturated hydrocarbon group having 2 to 12 carbon atoms, the saturated hydrocarbonic group may have a branch. As specific examples of the bivalent saturated hydrocarbonic group, there can be mentioned an ethylene group, a propylene group, an isopropene group, a hexylene group, a decylene group, a dodecylene group, etc., and among them alkylene groups having 5 to 10 carbon atoms are preferred in view of adhesive strength and the easiness of synthesis. In the group represented by the above general formula (III-2), n is an integer of 1 to 5. In the group represented by the above general formula (III-3), o and p each are an integer of 1 to 10, and it is preferred that they each are an integer of 3 to 6 in view of adhesive strength and the easiness of synthesis. In the group represented by the above general formula (III-3), q is an integer of 1 to 5, and it is preferred that it is an integer of 1 to 3 in view of adhesive strength and the easiness of synthesis. Further, in the group represented by the above general formula (III-4), r and s each are an integer of 1 to 5, and it is preferred that they each are an integer of 1 to 3 in view of adhesive strength and the easiness of synthesis.

In the above formula (I-1), Z represents a —COO— group, a —CH₂O— group or a —C₆H₄—CH₂O— group. Among them, a —COO— group is preferred in view of polymerizablity, the easiness of handling, etc.

Among the above thiouracil derivatives, those wherein in the formula (II), $R^1$ and $R^2$ each are a hydrogen atom or an alkyl group having 1 to 4 carbon atoms (provided that at least one of $R^1$ and $R^2$ is a hydrogen atom), and $R^3$ is a hydrogen atom, an alkyl group having 1 to 4 carbon atoms or a phenyl group, the spacer residue is an alkylene group having 5 to 10 carbon atoms or a group represented by the above general formula (III-2), (III-3) or (III-4) (provided that in these formulae, n is an integer of 1 to 5, o and p each are an integer of 3 to 6, q is an integer of 1 to 3, and r and s each are an integer of 1 to 3), $R^5$ is a hydrogen atom or a methyl group, and Z is a —COO— group are particularly preferred in view of adhesive strength, the easiness of synthesis and the easiness of handling.

Thus, preferred unsaturated thiouracil derivatives in the invention can also be represented by the following general formula (1) or (2)

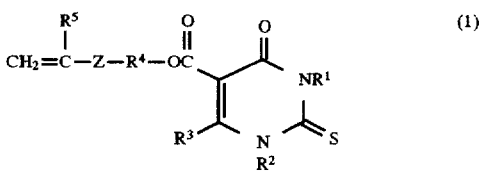 (1)

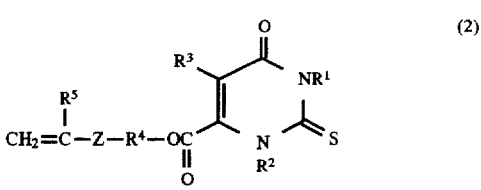 (2)

{wherein $R^1$ and $R^2$ each are a hydrogen atom or an alkyl group, and at least one of $R^1$ and $R^2$ is a hydrogen atom, $R^3$ is a hydrogen atom, an alkyl group or a phenyl group, and $R^4$ is a bivalent saturated hydrocarbon group having 2 to 12 carbon atoms, or any group selected from the following formulae (3), (4) and (5)

  (3)

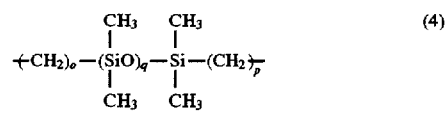  (4)

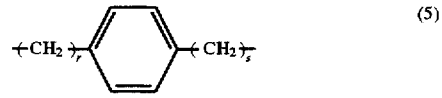  (5)

(wherein n is an integer of 1 to 5, o and p each are an integer of 1 to 10, q is an integer of 1 to 5, and r and s each are an integer of 1 to 5), Z is a —COO— group, a —CH₂O— group or a —C₆H₄—CH₂O— group, and $R^5$ is a hydrogen atom or a methyl group.}

Specific examples of the thiouracil derivative of the invention are as follows.

5 6
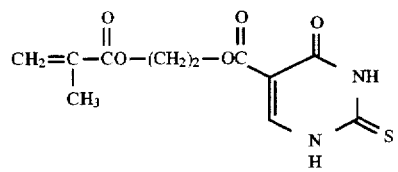 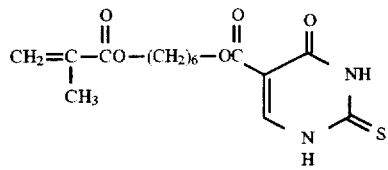
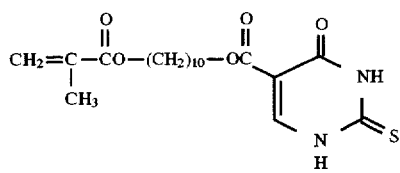 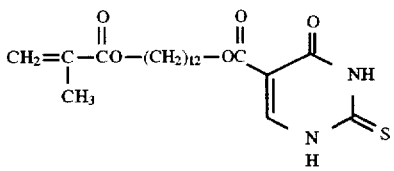
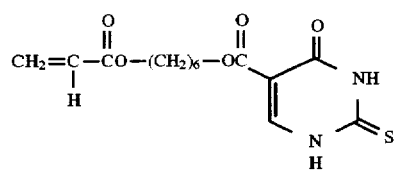 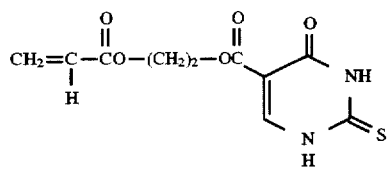
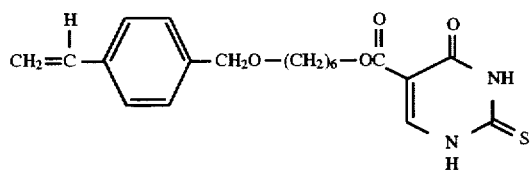 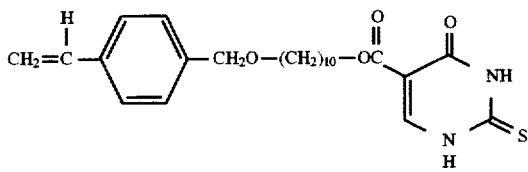
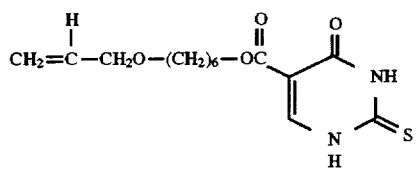 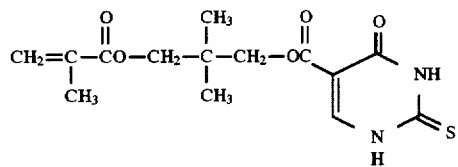
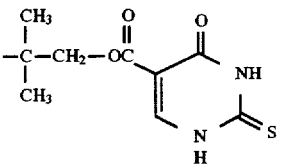
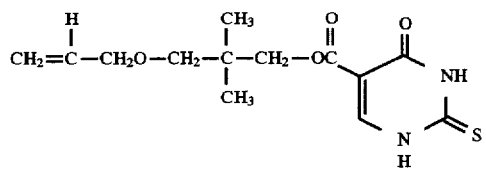 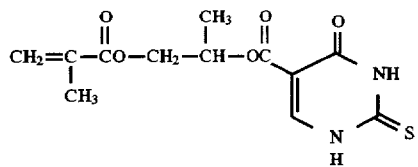
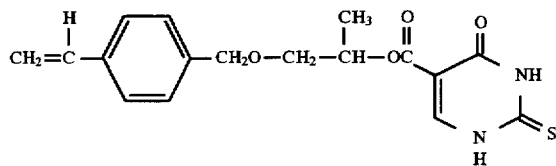 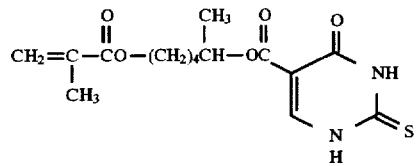
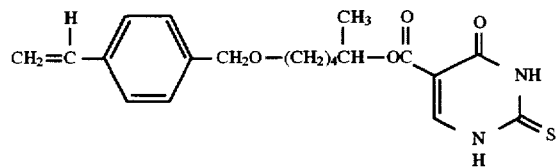 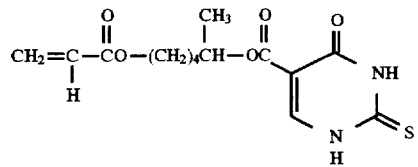

-continued
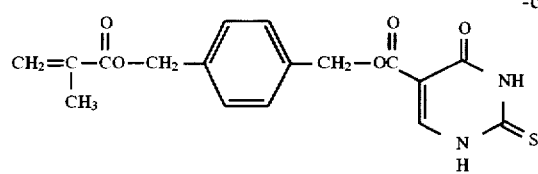
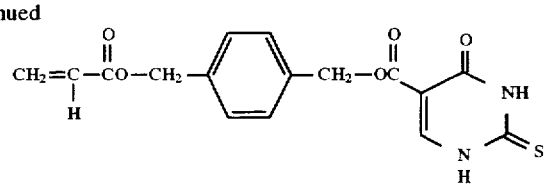
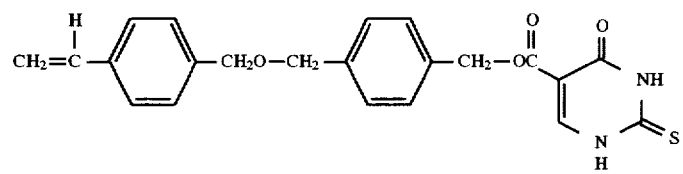
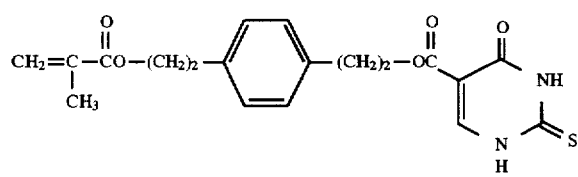
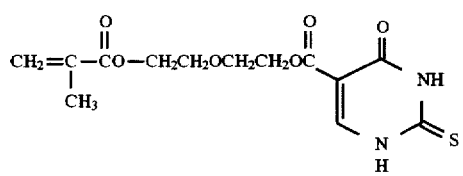
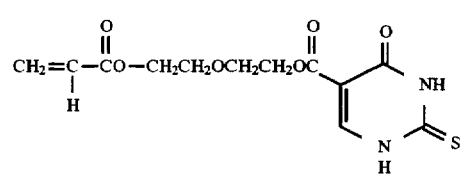
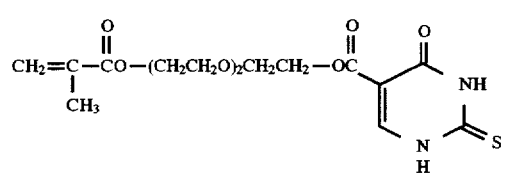
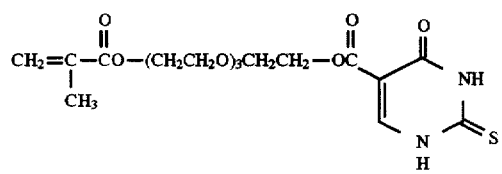
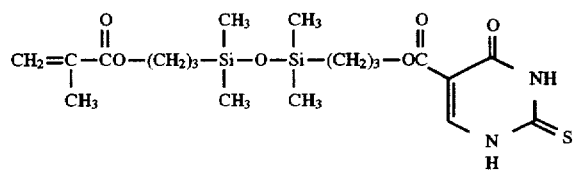
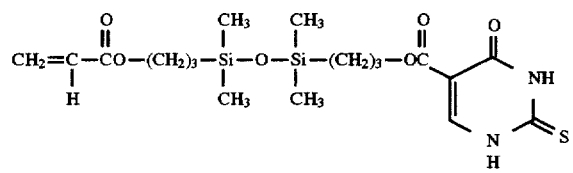
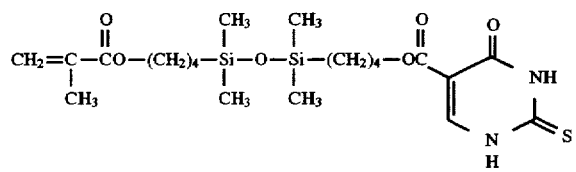
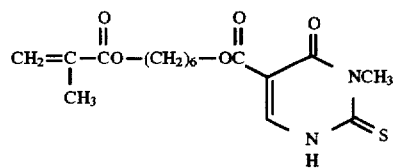
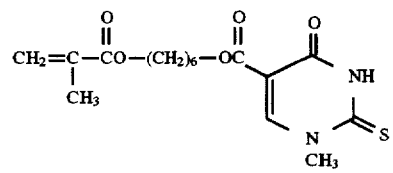
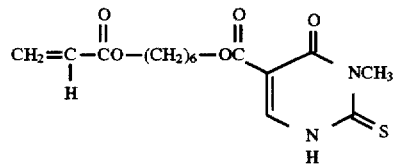
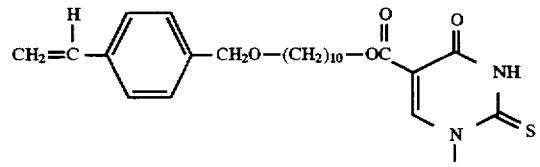
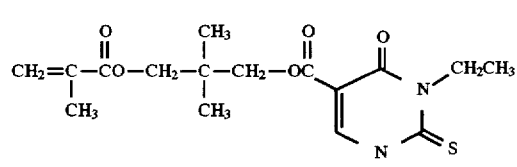
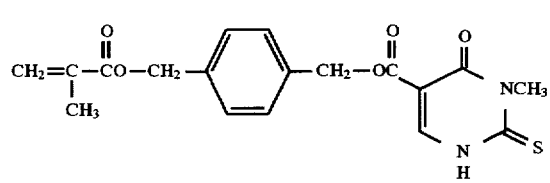

-continued
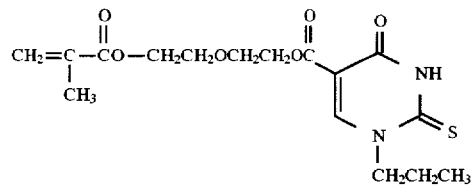
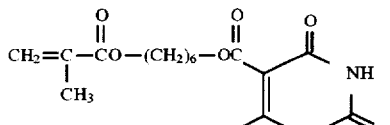
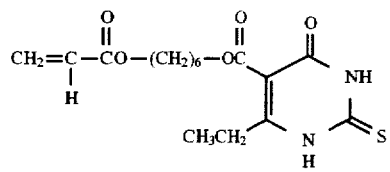
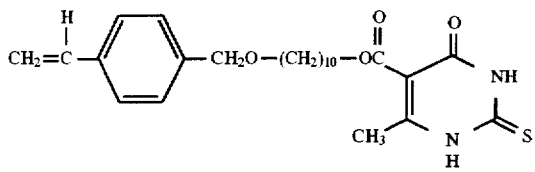
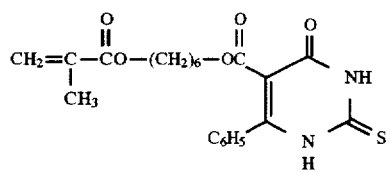
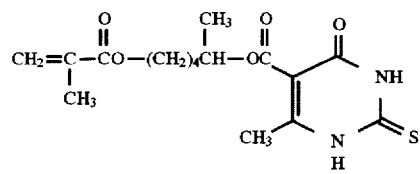
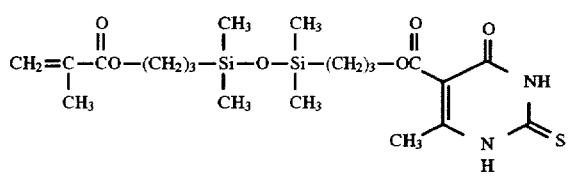
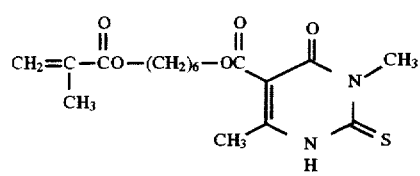
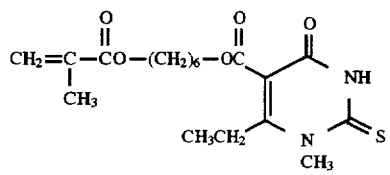
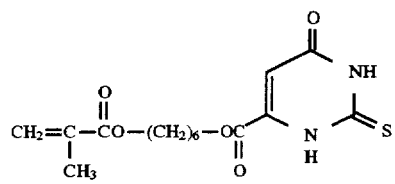
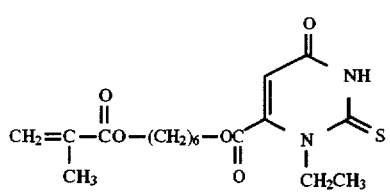
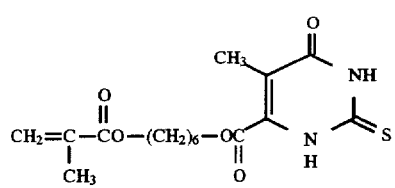
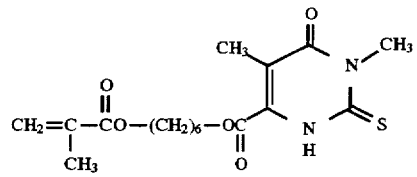
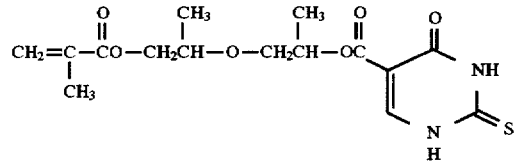
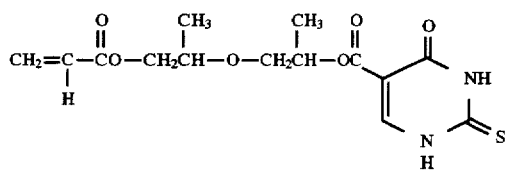
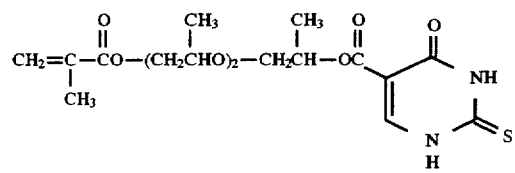
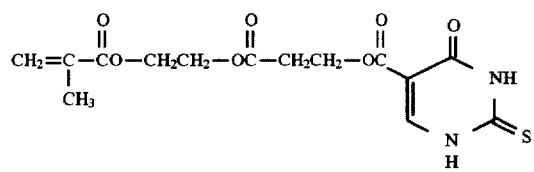
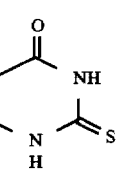

-continued

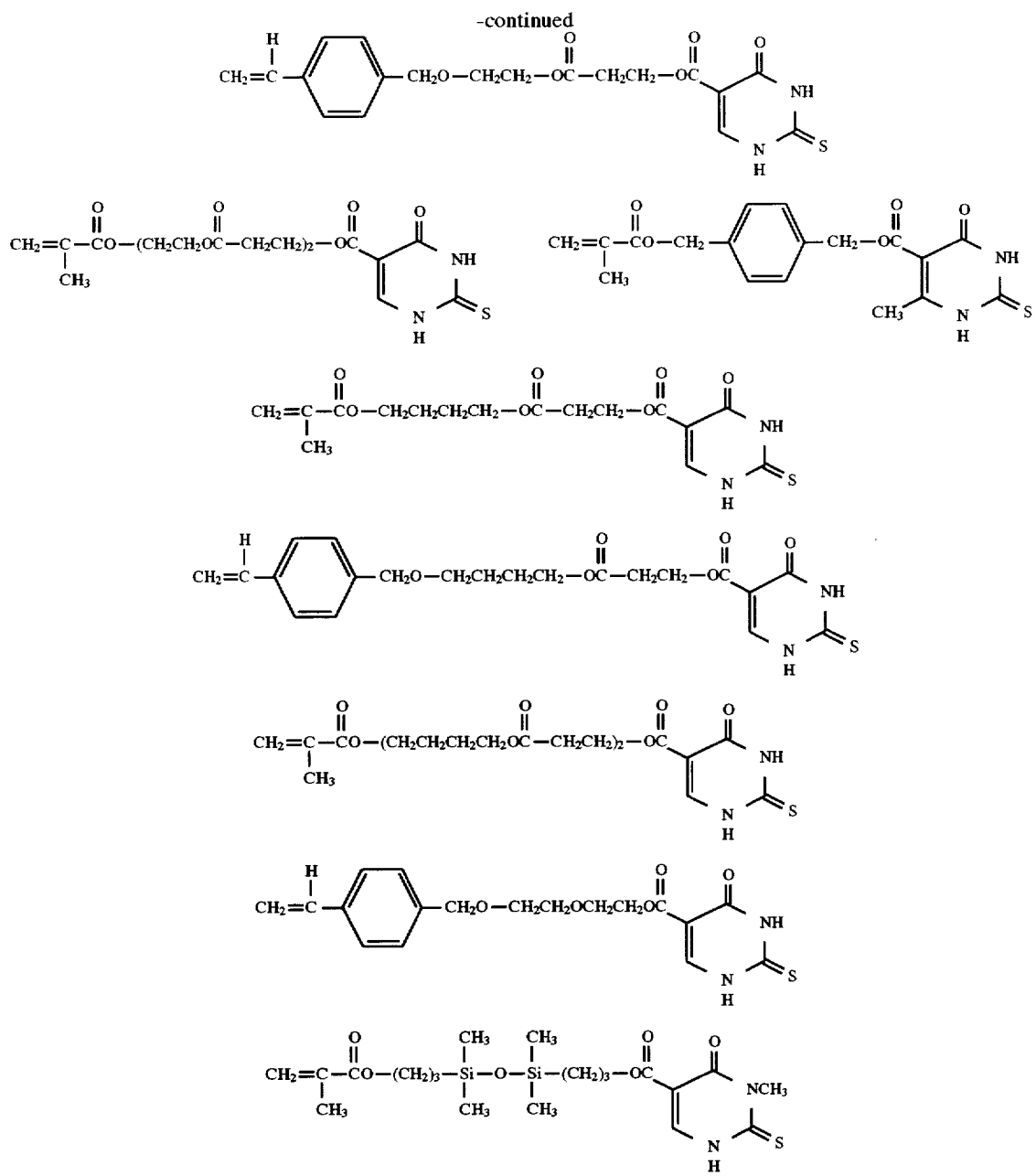

A process for producing a thiouracil derivative represented by the above general formula (1) or (2) is not particularly limited, and any process therefor can be adopted. A specific example of an industrially preferred process therefor is as follows.

First, description is made on a process for producing a thiouracil derivative represented by the above general formula (1). Namely, a thiouracil derivative having a polymerizable unsaturated bond of the above general formula (1) can be obtained by condensation reacting a thiourea derivative represented by the following general formula (6)

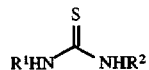
(6)

(wherein, $R^1$ and $R^2$ each are a hydrogen atom or an alkyl group, and at least one of $R^1$ and $R^2$ is a hydrogen atom) with a malonic acid derivative represented by the following general formula (7)

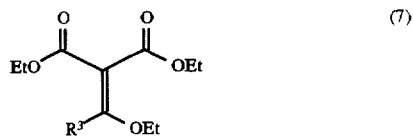
(7)

(wherein, $R^3$ is a hydrogen atom, an alkyl group or a phenyl group) to give a carbethoxythiouracil derivative represented by the following general formula (8)

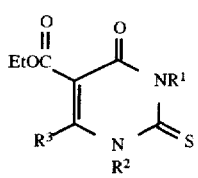

(8)

(wherein, R¹, R² and R³ are as defined in the above general formulae (6) and (7)), subjecting the derivative (8) to deesterification reaction to give a carboxythiouracil derivative represented by the following general formula (9)

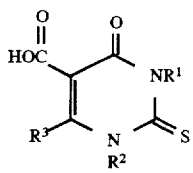

(9)

(wherein, R¹ R² and R³ are as defined in the above general formulae (6) and (7)), and reacting the derivative (9) with an alcohol having a polymerizable unsaturated bond represented by the following general formula (10)

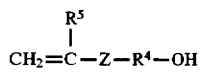

(10)

{wherein, R⁴ is a bivalent saturated hydrocarbon group having 2 to 12 carbon atoms, or any group selected from the following formulae (3), (4) and (5)

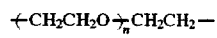

(3)

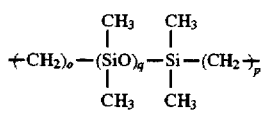

(4)

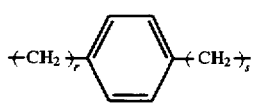

(5)

(wherein n is an integer of 1 to 5, o and p each are an integer of 1 to 10, q is an integer of 1 to 5, and r and s each are an integer of 1 to 5), Z is a —COO— group, a —CH₂O— group or a —C₆H₄—CH₂O— group, and R⁵ is a hydrogen atom or a methyl group.}.

As the thiourea derivative represented by the above general formula (6), known ones can be used without limitation. For example, thiourea, methylthiourea, ethylthiourea, propylthiourea, butylthiourea, etc. can preferably be used.

The malonic acid derivative represented by the general formula (7) can be synthesized by reacting diethyl malonate with an ortho acid triethyl.

As the ortho acid triethyl, there can be exemplified triethyl orthoformate, triethyl ortho-acetate, triethyl orthopropionate, triethyl orthobenzoate, etc.

More specifically, a malonic acid derivative represented by the general formula (7) can be obtained by putting 1 mol of diethyl malonate and 2 to 3 mols of sodium ethoxide in the presence of a solvent, and slowly adding dropwise 1 mol of an ortho acid triethyl to react them.

As to an alcohol having a polymerizable unsaturated bond represented by the above general formula (10), when Z is —COO— group, the alcohol can be obtained by esterification reaction between (meth)acrylic acid and a glycol, by esterification reaction between (meth)acryloyl chloride and a glycol, or the like. When Z is —CH₂O— group, such an alcohol can be obtained by reaction between allyl chloride and a glycol, or the like. When Z is a —C₆H₄—CH₂O— group, such an alcohol can be obtained by reaction between 4-vinylbenzyl chloride and a glycol, or the like.

As the glycol, there can be exemplified ethylene glycol, propylene glycol, pentamethylene glycol, hexamethylene glycol, octamethylene glycol, decamethylene glycol, dodecamethylene glycol, neopentyl glycol, 1,2-propanediol, 1,2-butanediol, 1,5-hexanediol, P-xylene glycol, diethylene glycol, 1,3-bis(3-hydroxypropyl)-1,1,3,3-tetramethyldisiloxane, 1,3-bis(4-hydroxybutyl)-1,1,3,3-tetramethyldisiloxane, etc.

More specifically, when Z in the general formula (10) is a —COO— group, a corresponding alcohol (10) can be obtained by feeding 1 mol of (meth)acrylic acid, 1 to 4 mols of a glycol and 0.01 to 0.1 mol of an acid catalyst, and reacting them. As the acid catalyst, p-toluenesulfonic acid, benzenesulfonic acid, etc. can preferably be used.

The alcohol (10) can also be obtained by feeding 1 to 4 mols of a glycol , and 1 mol of a tertiary amine or molecular sieve 3A as a dehydrohalogenating agent in the presence of a solvent, and slowly adding dropwise 1 mol of (meth) acryloyl chloride to cause esterification reaction. As the tertiary amine, pyridine, triethylamine, etc. can preferably be used.

When Z in the general formula (10) is a —CH₂O— group, a corresponding alcohol (10) can be obtained by feeding 1 to 4 mols of a glycol and 1 to 1.2 mols of a basic catalyst in the presence of a solvent, and slowly adding dropwise 1 mol of allyl chloride to cause reaction. As the basic catalyst, sodium hydride, etc. can preferably be used.

When Z in the general formula (10) is a —C₆H₄—CH₂O— group, a corresponding alcohol (10) can be obtained by feeding 1 to 2 mols of a glycol and 1 to 1.2 mols of a basic catalyst in the presence of a solvent, and slowly adding dropwise 1 mol of 4-vinylbenzyl chloride to cause reaction. As the basic catalyst, sodium hydride, etc. can preferably be used.

In these cases, both of a monosubstitution product (10) and a disubstitution product are obtained as the products. The monosubstitution product (10) can be separated and purified by distillation or column chromatography.

In the condensation reaction between the thiourea derivative of the general formula (6) and the malonic acid derivative of the general formula (7), the reaction molar ratio of the malonic acid derivative of the general formula (7) to the thiourea derivative of the general formula (6) is preferably 0.5 to 1.5.

As a reaction catalyst used at the time, a known one is usable, and sodium ethoxide , etc. can be exemplified, and its addition amount is preferably 0.5 to 1.5 times the molar amount of the thiourea derivative of the general formula (6).

As a solvent used in the reaction, ethanol, etc. can be mentioned. The temperature of the reaction can be selected from the range of 40° to 80° C., preferably from the range of 60° to 80° C. The reaction time is not particularly limited, and can generally be selected from the range of the order of 1 to 10 hours, but can be determined in accordance with the reaction temperature.

After the reaction, the salt deposited is dissolved in water, and an acid is added to make the solution acidic, whereby a carbethoxythiouracil derivative represented by the general formula (8) can be obtained.

In this connection, when, in the thiourea of the general formula (6), one of R¹ and R² is an alkyl group, the carbethoxythiouracil derivative of the general formula (8) is obtained as a mixture of isomers based on the substitution position on the N atoms of the alkyl group. These isomers can be separated and purified by column chromatography.

In the deesterification reaction of the carbethoxythiouracil derivative of the general formula (8) obtained by the reaction between the thiourea derivative of the general formula (6) and malonic acid derivative of the general formula (7), as the deesterifying agent to be used, a known one can be used, but a dimethyl sulfoxide solution of potassium tertiary butoxide is preferably used. The addition amount of the deesterifying agent is preferably in the range of 6 to 20 times the molar amount of the carbethoxythiouracil derivative, and more preferably in the range of 12 to 16 times the molar amount thereof.

The temperature of the reaction can be selected from the range of room temperature to 80° C., but preferably from the range of room temperature to 40° C. The reaction time is not particularly limited, and can generally be selected from the range of the order of 1 to 24 hours, but can be determined in accordance with the reaction temperature.

After the reaction, water is added to the reaction mixture, and further an acid is added to make the solution acidic, whereby a carboxythiouracil derivative represented by the general formula (9) can be obtained.

In the reaction between the carboxythiouracil derivative of the general formula (9) and the alcohol having a polymerizable unsaturated bond of the general formula (10), the reaction molar ratio of the alcohol having a polymerizable unsaturated bond of the general formula (10) to the carboxythiouracil derivative of the general formula (9) can be in the range of 1 to 5, but preferably in the range of 1 to 3.

As an esterifying catalyst for the esterification reaction to be used, there can be mentioned p-toluenesulfonic acid, benzenesulfonic acid, N,N'-dicyclohexylcarbodiimide, etc. The addition amount of the reaction catalyst is preferably in the range of 0.1 to 1 times the molar amount of the carboxythiouracil derivative.

As a solvent to be used in the reaction, there can be mentioned tetrahydrofuran, acetone, toluene, etc. Further, it is preferred to add a small amount of a polymerization inhibitor such as hydroquinone, hydroquinone monomethyl ether or butylhydroxytoluene.

The temperature of the reaction can be selected from the range of room temperature to 80° C., but preferably from the range of room temperature to 70° C. The reaction time is not particularly limited, and can generally be selected from the range of the order of 1 to 50 hours, but can be determined in accordance with the reaction temperature and in such a range that the polymerization does not take place.

After the reaction, the matter deposited is filtered out, the solvent is distilled off from the filtrate under reduced pressure, and the resultant concentrate is passed through a silica gel column using an inert solvent such as ethyl acetate as a developing solvent to carry out separation and purification, whereby a product having high purity can be obtained.

Next, description is made on a process for producing a thiouracil derivative represented by the general formula (2).

Namely, a thiouracil derivative having a polymerizable unsaturated bond of the general formula (2) can be obtained by condensation reacting a thiourea derivative represented by the general formula (6)

(wherein, $R^1$ and $R^2$ are as defined above) with a succinic acid derivative represented by the general formula (11)

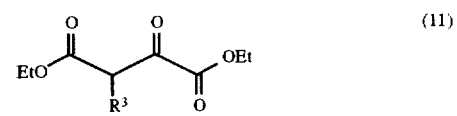

(wherein, $R^3$ is a hydrogen atom, an alkyl group or a phenyl group) to give a carbethoxythiouracil derivative represented by the general formula (12)

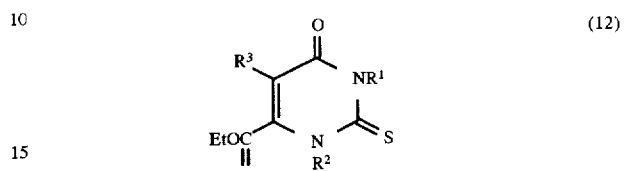

(wherein, $R^1$, $R^2$ and $R^3$ are as defined in the above general formulae), subjecting the carbethoxythiouracil derivative (12) to deesterification reaction to give a carboxythiouracil derivative represented by the general formula (13)

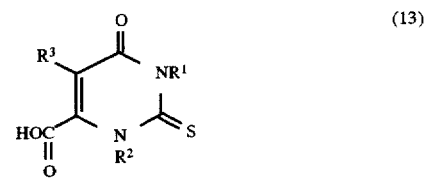

(wherein, $R^1$, $R^2$ and $R^3$ are as defined in the above general formulae), and then reacting the carboxythiouracil derivative (13) with an alcohol represented by the following general formula (10)

{wherein, $R^4$ is a bivalent saturated hydrocarbon group having 2 to 12 carbon atoms, or any group selected from the following general formula (3), (4) and (5)

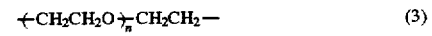

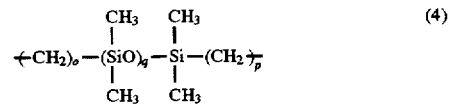

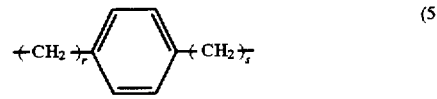

(wherein, n is an integer of 1 to 5, o and p each are an integer of 1 to 10, q is an integer of 1 to 5, and r and s each are an integer of 1 to 5), Z is a —COO— group, a —CH$_2$O— group or a —C$_6$H$_4$—CH$_2$O— group, and $R^5$ is a hydrogen atom or a methyl group}.

As the thiourea derivative represented by the above general formula (6), known ones can be used without limitation, as in the case of the preparation of the above general formula (1).

As the succinic acid derivative represented by the above general formula (11), known ones can be used without limitation. For example, there can preferably be used diethyl 2-oxosuccinate, diethyl 2-methyl-2'-oxosuccinate, diethyl 2-ethyl-2'-oxosuccinate, diethyl 2-butyl-2'-oxosuccinate, etc.

As the alcohol having a polymerizable unsaturated bond represented by the above general formula (10), there can be used the same ones as in the case of the preparation of the above general formula (1).

In the condensation reaction between the thiourea derivative of the above general formula (6) and the succinic acid derivative of the above general formula (11), the reaction molar ratio of the succinic acid derivative of the general formula (11) to the thiourea derivative of the general formula (6) is preferably 0.5 to 1.5.

As a reaction catalyst to be used at the time, known ones can be used, and sodium ethoxide, etc. are exemplified, and its addition amount is preferably 0.5 to 1.0 times the molar amount of the thiourea derivative of the general formula (6).

As a solvent used in the reaction, ethanol, etc. can be mentioned. The temperature of the reaction can be selected from the range of 40° to 80° C., preferably from the range of 60° to 80° C. The reaction time is not particularly limited, and generally can be selected from the range of the order of 1 to 10 hours, but can be determined in accordance with the reaction temperature.

After the reaction, the salt deposited is dissolved in water, and an acid is added to make the solution acidic, whereby a carbethoxythiouracil derivative represented by the general formula (12) can be obtained.

In this connection, when, in the thiourea of the general formula (6), one of $R^1$ and $R^2$ is an alkyl group, the carbethoxythiouracil derivative of the general formula (12) is obtained as a mixture of isomers based on the substitution position on the N atoms of the alkyl group. These isomers can be separated and purified by column chromatography.

The deesterification reaction of the carbethoxythiouracil derivative of the general formula (12) obtained by the reaction between the thiourea derivative of the general formula (6) and the succinic acid derivative of the general formula (11) can be carried out in the same manner as in the case of the carbethoxythiouracil derivative represented by the general formula (8).

The reaction between the carboxythiouracil derivative represented by the general formula (13) and the alcohol having a polymerizable unsaturated bond of the general formula (10) can be carried out in the same manner as in the reaction between the carboxythiouracil derivative of the general formula (9) and the alcohol having a polymerizable unsaturated bond of the general formula (10).

A thiouracil derivative having a polymerizable unsaturated bond represented by the general formula (1) or (2) can preferably be used as a component of an adhesive which bonds a noble metal, for example a dental noble metal alloy to a resin, and in such an occasion, it is preferred to use the thiouracil derivative as a solution in an organic solvent. As organic solvents used preferably therefor, general organic solvents or polymerizable monomers can be used without any limitation so long as they can dissolve the thiouracil derivative. However, when the organic solvents are nonvolatile, it gets difficult to exert the effects of the invention without heightening the concentration of the thiouracil derivative, and therefore, it is preferred to use organic solvents having volatility.

In the metal surface-treating agent of the invention, the concentration of the thiouracil derivative is not particularly limited, but in view of adhesive strength and the prevention of excess use, it is preferred that the concentration is in the range of 0.001 to 20% by weight. The further preferred concentration range of the thiouracil derivative is 0.005 to 10% by weight.

As specific examples of the organic solvents usable preferably, there can be mentioned alcohols such as methanol, ethanol, isopropyl alcohol and butanol; ketones such as acetone and methyl ethyl ketone; ethers such as ethyl ether, 1,4-dioxane and tetrahydrofuran; esters such as ethyl acetate and ethyl formate; aromatic solvents such as toluene, xylene and benzene; hydrocarbon solvents such as pentane, hexane, heptane and octane; chlorine solvents such as methylene chloride, chloroform and 1,2-dichloroethane; fluorine solvents such as trifluoroethanol; etc. Among them, acetone, toluene, ethanol, etc. are particularly preferably used in view of solubility, storage stability, etc.

Polymerizable monomers preferably usable as organic solvents in the invention are, for example, ones showing radical polymerizability. As specific examples of the polymerizable monomers usable preferably, there can be mentioned styrene and acrylic or methacrylic polymerizable monomers having high polymerizability such as methyl (meth)acrylate, ethyl (meth)acrylate, isopropyl (meth)acrylate, butyl (meth)acrylate and hydroxyethyl (meth)acrylate, etc.

The above organic solvents can be used alone or in combination of two or more.

In the metal surface-treating agent of the invention, in order to further heighten adhesiveness to base metals, it is also possible to further compound an acidic group-containing (meth)acrylate monomer. By using a metal surface-treating agent of such an embodiment, it gets possible to bond well a base metal such as a cobalt-chromium alloy or a nickel-chromium alloy to a resin or the like. Particularly, when a metal surface-treating agent of the embodiment is used to an alloy composed of base metal(s) and noble metal(s), the adhesive strength of the resultant composite gets higher than that obtained when a metal surface-treating agent wherein an acidic group-containing (meth)acrylate monomer is not compounded is used. Since alloys each composed of base metal(s) and noble metal(s) are often used for dental uses, metal surface-treating agents of the above embodiment are particularly effective as dental metal surface-treating agents.

The above acidic group-containing (meth)acrylate monomer is not particularly limited so long as it is a (meth)acrylate monomer having in the molecule acidic group(s) such as carboxyl group(s) or anhydride(s) thereof, or phosphoric acid group(s), and can be a known one, but is preferably an acidic group-containing (meth)acrylate monomer represented by the following general formula (14)

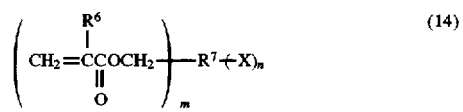

$$m = 1\text{--}4 \quad n = 1, 2$$

(wherein, $R^6$ represents a hydrogen atom or a methyl group, $R^7$ represents a bivalent to hexavalent organic residue having 1 to 20 carbon atoms optionally having ether linkage(s) and/or ester linkage(s), and X represents a group containing carboxyl group(s), anhydrous carboxyl group(s), phosphoric acid group(s) or phosphoric ester group(s)).

In the above general formula, X is a group containing carboxyl group(s), anhydrous carboxyl group(s), phosphoric acid group(s) or phosphoric ester group(s), and its structure is not particularly limited, but preferred specific examples thereof are as follows.

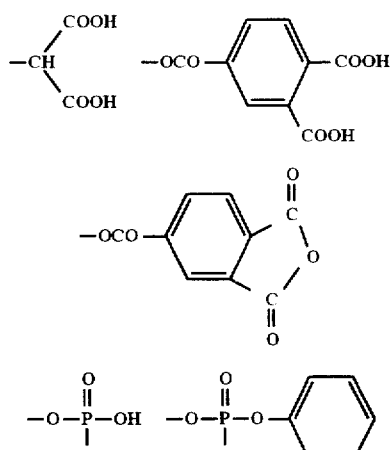

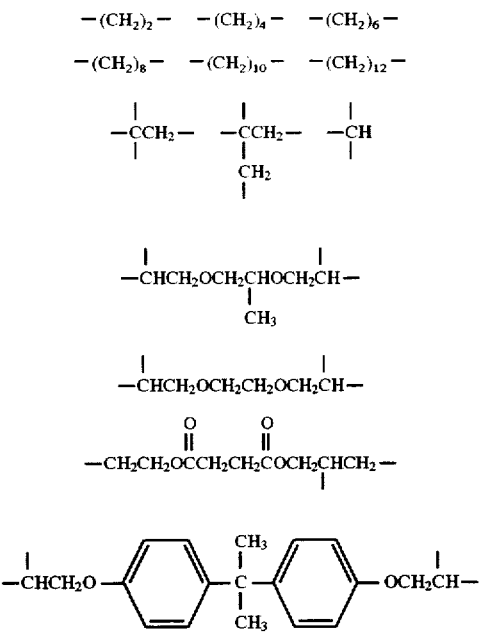

In the above general formula, the structure of R⁷ is not particularly limited, and can be known a bivalent to hexavalent organic residue having 1 to 20 carbon atoms optionally having ether linkage(s) and/or ester linkage(s), and specific examples thereof are as follows.

Preferred specific examples of the acidic group-containing (meth)acrylate monomer represented by the above general formula are as follows.

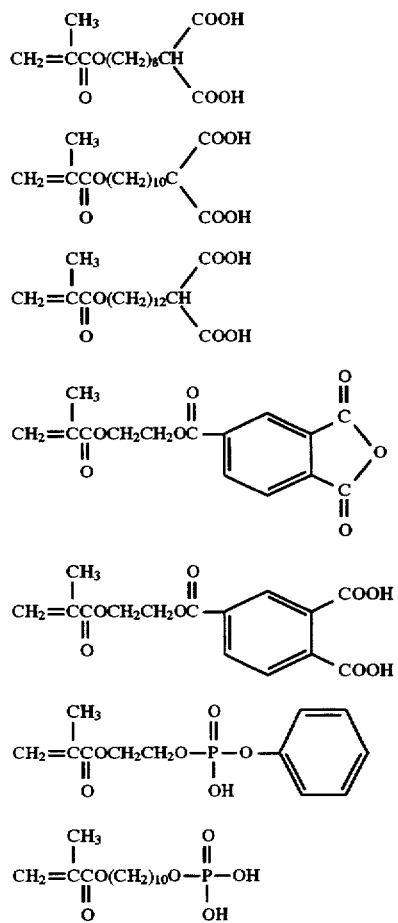

-continued
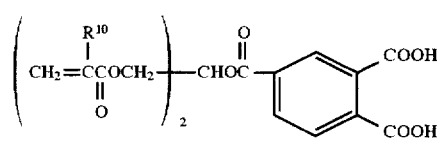
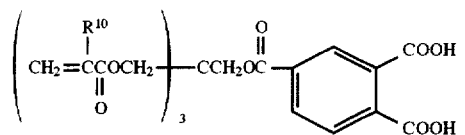
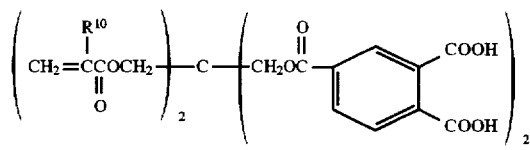
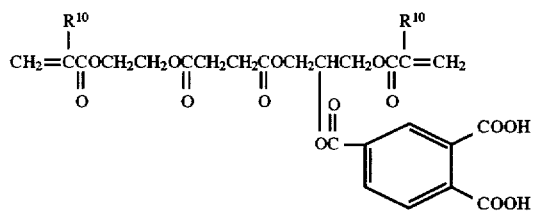
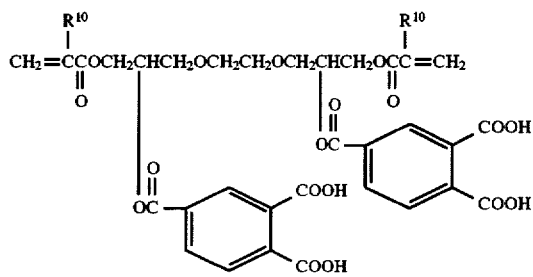
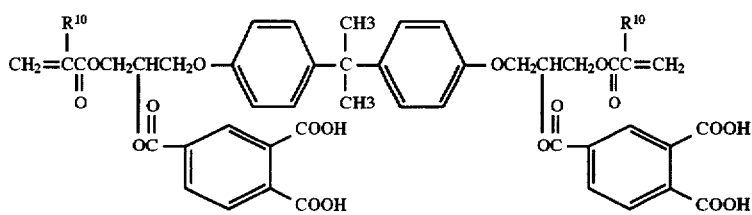
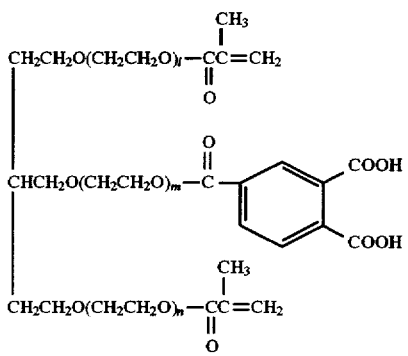
$l + m + n = 3.5$

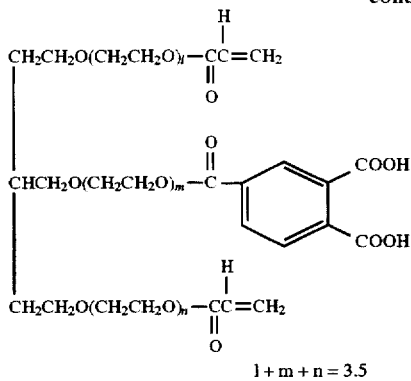

$l + m + n = 3.5$ (wherein, $R^6$ is a hydrogen atom or a methyl group) In view of adhesiveness to metals, among acidic group-containing (meth)acrylate monomers exemplified above as specific examples, those having carboxyl group(s) or phosphoric acid group(s) are used particularly preferably.

The above acidic group-containing (meth)acrylate monomers can be used alone or in combination of two or more.

In the metal surface-treating agent containing the acidic group-containing (meth)acrylate monomer, the compounding rate of the thiouracil derivative (a), the acidic group-containing (meth)acrylate monomer (b) and the organic solvent (c) is not particularly limited, but when the total of (a), (b) and (c) is supposed to be 100 weight parts, if the compounding amount of (a) is 0.001 to 20 weight parts, the compounding amount of (b) is 0.1 to 15 weight parts and (c) is the residual parts, good adhesion is made on both base metals and noble metals. A further preferred compounding rate is that (a) is 0.005 to 10 weight parts, (b) is 1 to 10 weight parts and (c) is the residual parts.

In the metal surface-treating agent of the invention, it is preferred in view of adhesive strength and the easiness of handling to use a thiouracil derivative represented by the general formula (1) or (2) in combination with an organic solvent capable of dissolving the thiouracil derivative and having volatility. Further, when it is desired to heighten adhesiveness to base metals, it is preferred to use the metal surface-treating agent in such a form that an acidic group-containing (meth)acrylate monomer represented by the general formula (14) is compounded therein.

Further, it is also possible, if necessary, to incorporate a polymerization catalyst in the metal surface-treating agent of the invention in such a range that adhesive strength is not lowered. As polymerization catalysts capable of being added, there can be mentioned peroxide polymerization catalysts, for example, diacyl peroxides such as benzoyl peroxide and decanoyl peroxide, dialkyl peroxides such as dicumyl peroxide and ditertiary butyl peroxide; barbituric acid polymerization catalysts such as 5-butylbarbituric acid and 5-butyl-2-thiobarbituric acid; α-diketones such as camphorquinone and acetylbenzoyl; benzoin alkyl ethers such as benzoin ethyl ether; thioxanthone derivatives such as 2-chlorothioxanthone and methylthioxanthone; photopolymerization catalysts, for example, benzophenone and benzophenone derivatives such as p,p'-methoxybenzophenone; amine co-catalysts such as dimethylaminoethyl methacrylate, N,N-dimethyl-p-toluidine and ethyl p-dimethylaminobenzoate; etc. These polymerization catalysts and co-catalysts can be added alone or, if necessary, in combination of two or more.

Further if necessary, it is also possible to add a polymerization inhibitor such as hydroquinone monomethyl ether, hydroquinone or 4-tertiary butylphenol.

As to a process for mixing the above components to give a metal surface-treating agent, there is no particular limitation, and for example, the metal surface-treating agent can be prepared by weighing the thiouracil derivative, the organic solvent and, if necessary, the acidic group-containing (meth)acrylate monomer, and other optional component(s) and putting them in a vessel at a desired mutual ratio, and stirring and mixing the mixture until it gets uniform.

The use method of the metal surface-treating agent of the invention is not particularly limited, but for giving good adhesion between a metal and a resin or the like, a method which comprises coating the surface of the metal with the metal surface-treating agent of the invention, piling up a polymerizable composition on the metal surface, and curing the polymerizable composition can suitably be adopted. Further, by bonding another resin, metal, ceramics or the like onto the opposite side of the surface of the polymerizable composition contacting to the metal, it is also possible to indirectly bond the metal to such a material.

In the above method, as the polymerizable composition piled up on the metal surface after the treatment, a known polymerizable composition can be used without any limitation, but a polymerizable composition containing an acrylic or methacrylic polymerizable monomer as a main component and containing a polymerization initiator is preferred in view of polymerizability, easiness of handling, etc. Polymerizable compositions generally used in the dental field such as, for example, denture base resins, quick self-curing resins, hard resins, composite resins, resin cements, etc. can preferably be used since they each contain acrylic or methacrylic polymerizable monomer(s) and a polymerization initiator.

As specific examples of the acrylic or methacrylic polymerizable monomer(s), there can be mentioned monofunctional polymerizable monomers such as methyl (meth)acrylate, ethyl (meth)acrylate, hydroxyethyl (meth)acrylate and methacryloyloxyethyl propionate; polyfunctional polymerizable monomers such as triethylene glycol di(meth)acrylate, 2,2-bis(4-(3-methacryloyloxy-2-hydroxypropoxy)phenyl)propane, 2,2-bis(4-methacryloyloxyethoxyphenyl)propane, 1,6-hexanediol di(meth)acrylate, neopentyl glycol di(meth)acrylate, trimethylhexamethylene diisocyanate and pentaerythritol tri(meth)acrylate; adhesive polymerizable monomers such as 4-methacryloyloxyethoxycarbonylphthalic anhydride, 10-methacryloyloxydecyl dihydrogenphosphate, 10-methacryloyloxydecamethylenemalonic acid and 2-methacryloyloxyethyl 3'-methacryloyloxy-2'-(3,4-dicarboxybenzoyloxy)propyl succinate; etc. These can be used alone or in combination of two or more.

As specific examples of the polymerization initiation catalyst, there can be mentioned redox initiators such as benzoyl peroxide/ N,N-diethanol-p-toluidine; alkyl metal compounds such as a partial oxide of tributylborane; barbituric acid initiators such as n-butylbarbituric acid/copper chloride; and photo-polymerization initiation catalysts such as camphorquinone/N,N-dimethylaminoethyl methacrylate.

When the metal surface-treating agent of the invention is used to a pure metal such as gold, palladium, platinum, silver or copper, or a gold alloy, gold-silver-palladium alloy, silver alloy or the like for dental uses, its effect is particularly remarkable.

Thiouracil derivatives represented by the general formula (1) or (2) of the invention are novel compounds, and since the thiouracil derivatives are excellent in adhesiveness to noble metals, they are useful as adhesive components of metal surface-treating agents. Further, since they each have a polymerizable unsaturated bond and sulfur, they are utilizable as intermediates of pharmaceuticals, dyes, etc.

By using a metal surface-treating agent containing a thiouracil derivative having in the molecule at least one radical polymerizable unsaturated bond of the invention, it is possible to bond a metal, particularly a noble metal to a resin or the like in high adhesive strength, and in high water resistance and in high durability. Further, when a metal surface-treating agent wherein an acidic group-containing (meth)acrylate monomer is further compounded is used, it is possible to exert very excellent adhesiveness to any of a noble metal and a base metal. Particularly, when the metal surface-treating agent wherein an acidic group-containing (meth)acrylate monomer is compounded is applied to an alloy composed of base metal(s) and noble metal(s), adhesive strength is obtained too high to be anticipated from metal surface-treating agents wherein a thiouracil derivative and an acidic group-containing (meth)acrylate monomer are compounded respectively alone in organic solvents. Further, these metal surface-treating agents of the invention are high in storage stability and very excellent also in handling.

The detail of the reason why the above excellent effects are exerted is not clear at present, but is surmised as follows. Namely, when first the surface of a metal is coated with a metal surface-treating agent composed of a thiouracil derivative and an organic solvent, the surfur atoms in the thiouracil molecules immediately react with the metal atoms or the metal oxide on the surface whereby chemical bonds excellent in water resistance are formed. Then, when a polymerizable composition is piled up on the surface, the polymerizable unsaturated bond of the thiouracil derivative reacts with the polymerizable monomer in the polymerizable composition to cause copolymerization and curing, whereby strong linkage to the metal is formed. It is surmised that the above first reaction is particularly liable to occur on the surface of a noble metal, and as a result, good adhesion between the noble metal and the resin or the like gets possible.

On the other hand, it is surmised that as to an acidic group-containing (meth)acrylate monomer, its acidic group has a strong tendency to react with a base metal atom or an oxide thereof to form a chemical bond excellent in water resistance, and therefore, when the monomer is compounded, adhesive strength to the base metal is heightened. Further, it is surmised that when an alloy composed of base metal(s) and noble metal(s) is coated with a metal surface-treating agent wherein an acidic group-containing (meth)acrylate monomer is compounded, the above reaction and the above reactions by the thiouracil derivative simultaneously occur, and adhesive strength is enhanced by the synergistic effects of the time.

The present invention is further detailedly described by examples, but the invention should not be limited thereto.

EXAMPLE 1

Potassium tertiary butoxide (43.7 g, 389 mmol) and dimethyl sulfoxide (400 ml) were put in a 2-L egg-plant type flask to make a solution, ethyl 2-thiouracil-5-carboxylate (5.0 g, 25.0 mmol) was slowly added dropwise to the solution, and the mixture was subjected to reaction at room temperature for 1 hour. After the completion of the reaction, methanol (500 ml) was added to the reaction mixture, and the precipitate deposited was filtered. The resultant precipitate was dissolved in water, and hydrochloric acid was added to this solution to give 5-carboxy-2-thiouracil (2.54 g) as a light yellow solid.

2-hydroxyethylmethacrylate (3.90 g, 30 mmol), N,N'-dicyclohexylcarbodiimide (2.27 g, 11 mmol), 5-carboxy-2-thiouracil (1.72 g, 10 mmol) and tetrahydrofuran (50 ml) were put into 200 ml three-necked flask to make a solution, the solution was continuously stirred at room temperature for 3 days. As the reaction proceeded, a white precipitate was formed. After the reaction was completed, said white precipitate was filtered. Tetrahydrofuran was distilled off from the resultant filtrate under reduced pressure and then the residue was subjected to silica gel chromatography. 2-methacryloyloxyethyl 2-thiouracil-5-carboxylate |A| (0.91 g, 3.2 mmol) represented by following formula was obtained by using mixture of ethyl acetate and hexane as developing solvent. The result of NMR (d6DMSO), MASS and elementary analysis are shown below.

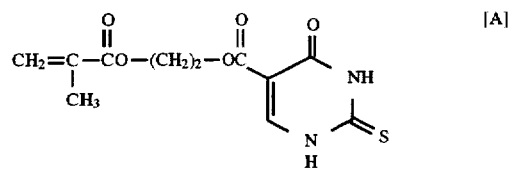

NMR (δ, ppm): 1.88 (3H, —$CH_3$)
4.36 (4H, —COO—$CH_2CH_2$—OCO—)
5.68, 6.03 (2H, $CH_2$=C—)
7.97 (1H, —N—CH=C—) 12.6 (2H, —NH—)
MASS (M+1)$^+$=285
Elementary analysis; $C_{11}H_{12}N_2O_5S$

|  | C | H | N |
|---|---|---|---|
| Calculated | 46.47 | 4.25 | 9.85 |
| Found | 46.45 | 4.26 | 9.83 |

EXAMPLE 2

Under an atmosphere of nitrogen, an acetonitrile solution (30 ml) of methacryloyl chloride (20.9 g, 0.2 mol) was slowly added dropwise at room temperature, using a dropping funnel, to 1,6-hexanediol (47.3 g, 0.40 mol), molecular sieve 3A powder (40 g) and acetonitrile (470 ml) in a 1-L three-necked flask. After the completion of the dropwise addition, the mixture was refluxed with heating for 5 hours. The mixture was then left alone to cool to room temperature, the molecular sieve 3A powder was filtered out from the reaction mixture, and acetonitrile was distilled off under reduced pressure from the filtrate. Methylene chloride (300 ml) was added to the residue, and the resultant methylene chloride solution was washed with water. The methylene chloride layer was dried over anhydrous sodium sulfate. and the solvent was distilled off under reduced pressure. 6-Hydroxyhexyl methacrylate (33.3 g) was separated and purified as a colorless transparent liquid from this residue by silica gel column chromatography.

6-Hydroxyhexyl methacrylate (5.59 g, 30 mmol), N,N'-dicyclohexylcarbodiimide (2.27 g, 11 mmol), 5-carboxy-2-thiouracil (1.72 g, 10 mmol) and tetrahydrofuran (50 ml) were put in a 200-ml three-necked flask to make a solution, and the solution was continuously stirred at room temperature for 3 days. A white precipitate was formed as the reaction progressed, and after the completion of the reaction, the white precipitate was filtered out. Then the same separation and purification operations were carried out as in Example 1 to give 6-methacryloyloxyhexyl 2-thiouracil-5-carboxylate |B| (1.13 g, 3.3 mmol) repre- sented by the following formula. The results of NMR (d6DMSO), MASS and elementary analysis are shown below.

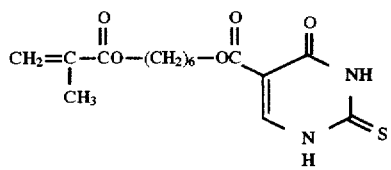

NMR (δ, ppm); 1.3-1.7 (8H, —COO—CH$_2$(CH$_2$)$_4$CH$_2$—OCO—)

1.87 (3H, —CH$_3$)

4.09, 4.13 (4H, —COO—CH$_2$(CH$_2$)$_4$CH$_2$—OCO—)

5.65, 6.01 (2H, CH$_2$=C—)

7.94 (1H, —N—CH=C—)

12.7 (2H, —NH—)

MASS (M+1)$^+$=341

Elementary analysis; C$_{15}$H$_{20}$N$_2$O$_5$S

|  | C | H | N |
| --- | --- | --- | --- |
| Calculated | 52.93 | 5.92 | 8.23 |
| Found | 52.96 | 5.92 | 8.25 |

EXAMPLE 3

Under an atmosphere of nitrogen, a tetrahydrofuran solution (30 ml) of methacryloyl chloride (10.5 g, 0.1 mol) was slowly added dropwise at room temperature, using a dropping funnel, to 1, 10-decanediol (34.9 g, 0.20 mol), molecular sieve 3A powder (20 g) and tetrahydrofuran (350 ml) in a 1-L three-necked flask. After the completion of the dropwise addition, the mixture was refluxed with heating for 5 hours. The mixture was then left alone to cool to room temperature, the molecular sieve 3A powder was filtered out from the reaction mixture, and tetrahydrofuran was distilled off under reduced pressure from the filtrate. Methylene chloride (300 ml) was added to the residue, and the resultant methylene chloride solution was washed with water. The methylene chloride layer was dried over anhydrous sodium sulfate, and the solvent was distilled off under reduced pressure. 10-Hydroxydecyl methacrylate (14.5 g) was separated and purified as a colorless transparent liquid from this residue by silica gel column chromatography.

10-Hydroxydecyl methacrylate (7.27 g, 30 mmol), N,N'-dicyclohexylcarbodiimide (2.27 g, 11 mmol), 5-carboxy-2-thiouracil (1.72 g, 10 mmol) and tetrahydrofuran (50 ml) were put in a 200-ml three-necked flask to make a solution, and the solution was continuously stirred at room temperature for 3 days. A white precipitate was formed as the reaction progressed, and after the completion of the reaction, the white precipitate was filtered out. Then, the same separation and purification operations as in Example 1 were carried out to give 10-methacryloyloxydecyl 2-thiouracil-5-carboxylate |C| (1.15 g, 2.9 mmol) represented by the following formula. The results of NMR (d6DMSO), MASS and elementary analysis are shown below.

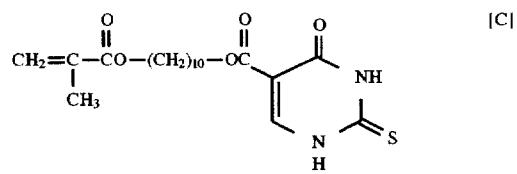

NMR (δ, ppm); 1.3-1.8 (16H, —COO—CH$_2$(CH$_2$)$_8$CH$_2$—OCO—)

1.87 (3H, —CH$_3$).

4.08, 4.13 (4H, —COO—CH$_2$(CH$_2$)$_8$CH$_2$—OCO—)

5.65, 6.01 (2H, CH$_2$=C—).

7.93 (1H, —N—CH=C—).

12.8 (2H, —NH—)

MASS (M+1)$^+$=397

Elementary analysis; C$_{19}$H$_{28}$N$_2$O$_5$S

|  | C | H | N |
| --- | --- | --- | --- |
| Calculated | 57.56 | 7.12 | 7.07 |
| Found | 57.51 | 7.14 | 7.08 |

EXAMPLE 4

Under an atmosphere of nitrogen, an acetonitrile solution (30 ml) of acryloyl chloride (18.1 g, 0.2 mol) was slowly added dropwise at room temperature, using a dropping funnel, to an acetonitrile solution (470 ml) of 1,6-hexanediol (47.3 g, 0.40 mol) and molecular sieve 3A powder (40 g) in a 1-L three-necked flask. After the completion of the dropwise addition, the mixture was refluxed with heating for 5 hours. After the reaction, the same treatment as in Example 2 was carried out, and thereafter, 6-hydroxyhexyl acrylate (28.9 g) was separated and purified as a colorless transparent liquid.

6-Hydroxyhexyl acrylate (5.17 g, 30.0 mmol), N,N'-dicyclohexylcarbodiimide (2.27 g, 11 mmol), 5-carboxy-2-thiouracil (1.72 g, 10 mmol) and tetrahydrofuran (50 ml) were put in a 200-mi three-necked flask to make a solution, and the solution was continuously stirred at room temperature for 3 days. A white precipitate was formed as the reaction progressed, and after the completion of the reaction, the white precipitate was filtered out. Then, the same separation and purification operations as in Example 1 to give 6-acryloyloxyhexyl 2-thiouracil-5-carboxylate |D| (1.01 g, 3.1 mmol) represented by the following formula. The results of NMR (d6DMSO), MASS and elementary analysis are shown below.

[Structure D: CH₂=C(H)-CO-O-(CH₂)₆-OC(=O)- attached to thiouracil ring]

$$\text{[D]}$$

NMR (δ, ppm); 1.3–1.7 (8H, —COO—CH₂(CH₂)₄CH₂—OCO—)

4.09, 4.13 (4H, —COO—CH₂(CH₂)₄CH₂—OCO—)

5.82, 6.12, 6.45 (3H, CH₂=CH—), 7.93 (1H, —N—CH=C—), 12.7 (2H, —NH—)

MASS (M+1)⁺=327

Elementary analysis; C₁₄H₁₈N₂O₅S

| | C | H | N |
|---|---|---|---|
| Calculated | 51.52 | 5.56 | 8.58 |
| Found | 51.56 | 5.57 | 8.57 |

EXAMPLE 5

Under an atmosphere of nitrogen, a tetrahydrofuran solution (30 ml) of 1,6-hexanediol (4.72 g, 40 mol) was slowly added dropwise at room temperature, using a dropping funnel, to a tetrahydrofuran solution (20 ml) of 60% sodium hydride (1.92 g, 48 mmol) in a 300-ml three-necked flask. Successively, a tetrahydrofuran solution (30 ml) of chloromethylstyrene (6.1 g, 40 mmol) was slowly added dropwise. After the completion of the dropwise addition, the mixture was refluxed with heating for 4 hours. The mixture was then left alone to cool to room temperature, and diluted hydrochloric acid was added to the reaction mixture to stop the reaction. The aqueous layer was extracted with ether, and the resultant organic layer combined was washed with aqueous saturated sodium hydrogencarbonate solution and saturated sodium chloride solution. The organic layer was dried over anhydrous magnesium sulfate, the solvent was distilled off under reduced pressure, and then 1-hydroxy-6-(p-vinylbenzyloxy)hexane (7.97 g) was separated and purified by silica gel column chromatography.

1-Hydroxy-6-(p-vinylbenzyloxy)hexane (7.03 g, 30 mmol), N,N'-dicyclohexylcarbodiimide (2.27 g, 11 mmol), 5-carboxy-2-thiouracil (1.72 g, 10 mmol) and tetrahydrofuran (50 ml) were put in a 200-ml three-necked flask to make a solution, and the solution was continuously stirred at room temperature for 3 days. A white precipitate was formed as the reaction progressed, and after the completion of the reaction, the white precipitate was filtered out. Then, the same separation and purification operations as in Example 1 were carried out to give 6-(p-vinylbenzyloxy)hexyl 2-thiouracil-5-carboxylate [E] (1.17 g, 3.0 mmol) represented by the following formula. The results of NMR (d6DMSO), MASS and elementary analysis are shown below.

[Structure E: CH₂=C(H)-C₆H₄-CH₂O-(CH₂)₆-OC(=O)- attached to thiouracil ring]

$$\text{[E]}$$

NMR (δ, ppm); 1.3–1.7 (8H, —COO—CH₂ (CH₂)₄CH₂—OCH₂—)

3.49, 4.1 (4H, —COO—CH₂(CH₂)₄CH₂—OCH₂—)

4.53 (2H, —OCH₂—C₆H₄)

5.27, 5.84, 6.71 (3H, CH₂=CH—), 7.3–7.4 (4H, C₆H₄)

7.93 (1H, —N—CH=C—), 12.7 (2H, —NH—)

MASS (M+1)⁺=389

Elementary analysis; C₂₀H₂₄N₂O₄S

| | C | H | N |
|---|---|---|---|
| Calculated | 61.84 | 6.23 | 7.21 |
| Found | 61.81 | 6.27 | 7.24 |

EXAMPLE 6

Under an atmosphere of nitrogen, a tetrahydrofuran solution (30 ml) of methacryloyl chloride (10.5 g, 0.1 mol) was slowly added dropwise at room temperature, using a dropping funnel, to 2,2-dimethyl-1,3-propanediol (20.8 g, 0.2 mol), molecular sieve 3A powder (20 g) and tetrahydrofuran (350 ml) in a 1-L three-necked flask. After the completion of the dropwise addition, the mixture was refluxed with heating for 4 hours. After the reaction, the same operations as in Example 3 were carried out, and thereby 3-hydroxy-2,2-dimethylpropyl methacrylate (13.1 g) was separated and purified.

3-Hydroxy-2,2-dimethylpropyl methacrylate (5.18 g, 30 mmol), N,N'-dicyclohexylcarbodiimide (2.27 g, 11 mmol), 5-carboxy-2-thiouracil (1.72 g, 10 mmol) and tetrahydrofuran (50 ml) were put in a 200 ml three-necked flask to make a solution, and the solution was continuously stirred at room temperature for 3 days. A white precipitate was formed as the reaction progressed, and after the completion of the reaction, the white precipitate was filtered out. Then, the same separation and purification operations as in Example 1 were carried out to give 3-methacryloyloxy-2,2-dimethylpropyl 2-thiouracil-5-carboxylate [F] (0.91 g, 2.8 mmol) represented by the following formula. The results of NMR (d6DMSO), MASS and elementary analysis are shown below.

[Structure F: CH₂=C(CH₃)-CO-O-CH₂-C(CH₃)₂-CH₂-OC(=O)- attached to thiouracil ring]

$$\text{[F]}$$

NMR (δ, ppm); 0.91 (6H, —CH₂C(CH₃)₂CH₂—)

1.87 (3H, CH₂=C—CH₃), 4.1, 4.18 (4H, —COO—CH₂C(CH₃)₂CH₂—OCO—)

5.66, 6.02 (2H, CH₂=C—)

7.93 (1H, —N—CH=C—), 12.8 (2H, —NH—)
MASS (M+1)⁺=327
Elementary analysis; $C_{14}H_{18}N_2O_5S$

|  | C | H | N |
|---|---|---|---|
| Calculated | 51.52 | 5.56 | 8.58 |
| Found | 51.54 | 5.55 | 8.57 |

EXAMPLE 7

Under an atmosphere of nitrogen, an acetonitrile solution (30 ml) of methacryloyl chloride (20.9 g, 0.2 mol) was slowly added dropwise at room temperature, using a dropping funnel, to acetonitrile solution (470 ml) of 1-methyl-1,5-pentanediol (47.3 g, 0.40 mol), molecular sieve 3A powder (40 9) in a 1-L three-necked flask. After the completion of the dropwise addition, the mixture was refluxed with heating for 5 hours. After the reaction, the same operations as in Example 2 were carried out, and thereby 5-hydroxy-5-methylpentylmethacrylate (29.4 g) as a colorless transparent liquid was separated and purified.

5-Hydroxy-5-methylpentyl methacrylate (5.59 g, 30 mmol), N,N'-dicyclohexylcarbodiimide (2.27 g, 11 mmol), 5-carboxy-2-thiouracil (1.72 g, 10 mmol) and tetrahydrofuran (50 ml) were put in a 200 ml three-necked flask to make a solution, and the solution was continuously stirred at room temperature for 3 days. A white precipitate was formed as the reaction progressed, and after the completion of the reaction, the white precipitate was filtered out. Then, the same separation and purification operations as in Example 1 were carried out to give 5-methacryloyloxy-1-methylpentyl 2-thiouracil-5-carboxylate [G] (0.71 g, 2.1 mmol) represented by the following formula. The results of NMR (d6DMSO), MASS and elementary analysis are shown below.

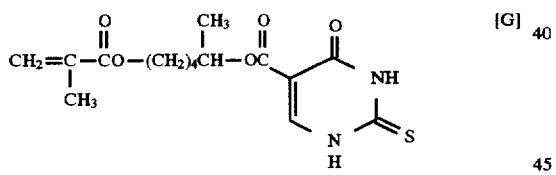

NMR (δ, ppm); 1.24 (3H, —OCH(CH₃)CH₂—)
1.3-1.7 (6H, —COO—CH(CH₂)₃CH₂—OCO—)
1.87 (3H, CH₂=C—CH₃),
4.69, 4.13 (3H, —COO—CH(CH₂)₃ CH₂—OCO—)
5.65, 6.01 (2H, CH₂=C—),
7.94 (1H, —N—CH=C—),
12.7 (2H, —NH—)
MASS (M+1)⁺=341
Elementary analysis; $C_{15}H_{20}N_2O_5S$

|  | C | H | N |
|---|---|---|---|
| Calculated | 52.93 | 5.92 | 8.23 |
| Found | 52.91 | 5.95 | 8.25 |

EXAMPLE 8

Under an atmosphere of nitrogen, an acetonitrile solution (30 ml) of methacryloyl chloride (20.9 g, 0.2 mol) was slowly added dropwise at room temperature, using a dropping funnel, to p-xylene glycol (55.2 g, 0.40 mol), molecular sieve 3A powder (40 g) and acetonitrile (470 ml) in a 1-L three-necked flask. After the completion of the dropwise addition, the mixture was refluxed with heating for 5 hours. Then, the reaction mixture was left alone to cool to room temperature, the molecular sieve 3A powder was filtered out from the reaction mixture, and acetonitrile was distilled off from the filtrate under reduced pressure. Methylene chloride (300 ml) was added to the residue, and the methylene chloride solution was washed with water. The resultant methylene chloride layer was dried over anhydrous sodium sulfate, and the solvent was distilled off under reduced pressure. 4-(Hydroxymethyl)benzyl methacrylate (34.8 g) was separated and purified as a white solid from this residue by silica gel column chromatography.

4-(Hydroxymethyl)benzyl methacrylate (6.48 g, 30 mmol), N,N'-dicyclohexylcarbodiimide (2.27 g, 11 mmol), 5-carboxy-2-thiouracil (1.72 g, 10 mmol) and tetrahydrofuran (50 ml) were put in a 200-ml three-necked flask to make a solution, and the solution was continuously stirred at room temperature for 3 days. A white precipitate was formed as the reaction progressed, and after the completion of the reaction, the white precipitate was filtered out. Then, the same separation and purification operations as in Example 1 were carried out to give 4-(methacryloyloxymethyl)benzyl 2-thiouracil-5-carboxylate [H]. (0.91 g, 2.5 mmol) represented by the following formula. The results of NMR (d6DMSO), MASS and elementary analysis are shown below.

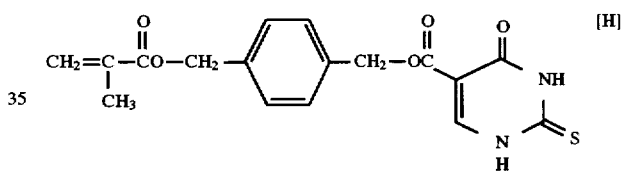

NMR (δ, ppm); 1.90 (3H, —CH₃),
5.17, 5.23 (4H, —COO—CH₂—C₆H₄—CH₂—OCO—)
5.70, 6.07 (2H, CH₂=C—),
7.40 (4H, —C₆H₄—),
8.00 (1H, —N—CH=C—),
12.8 (2H, —NH—)
MASS (M+1)⁺=361
Elementary analysis; $C_{17}H_{16}N_2O_5S$

|  | C | H | N |
|---|---|---|---|
| Calculated | 56.66 | 4.47 | 7.77 |
| Found | 56.42 | 4.31 | 7.82 |

EXAMPLE 9

Under an atmosphere of nitrogen, an acetonitrile solution (30 ml) of methacryloyl chloride (20.9 g, 0.2 mol) was slowly added dropwise at room temperature, using a dropping funnel, to diethylene glycol (42.4 g, 0.40 mol), molecular sieve 3A powder (40 g) and acetonitrile (470 ml) in a 1-L three-necked flask. After the completion of the dropwise addition, the mixture was refluxed with heating for 5 hours. Then, the reaction mixture was left alone to cool to room temperature, the molecular sieve 3A powder was filtered out from the reaction mixture, and acetonitrile was distilled off from the filtrate under reduced pressure. Methylene chloride (300 ml) was added to the residue, and the methylene chloride solution was washed with water. The resultant methylene chloride layer was dried over anhydrous sodium sulfate, and the solvent was distilled off under reduced pressure. Diethylene glycol monomethacrylate (59.2 g) was separated and purified as a colorless transparent liquid from this residue by silica gel column chromatography.

Diethylene glycol monomethacrylate (5.22 g, 30.0 mmol), N,N'-dicyclohexylcarbodiimide (2.27 g, 11 mmol), 5-carboxy-2-thiouracil (1.72 g, 10 mmol) and tetrahydrofuran (50 ml) were put in a 200-ml three-necked flask to make a solution, and the solution was continuously stirred at room temperature for 3 days. A white precipitate was formed as the reaction progressed, and after the completion of the reaction, the white precipitate was filtered out. Then, the same separation and purification operations as in Example 1 were carried out to give 2-(2-methacryloyloxyethoxy)ethyl 2-thiouracil-5-carboxylate [I] (1.05 g, 3.2 mmol) represented by the following formula. The results of NMR (d6DMSO), MASS and elementary analysis are shown below.

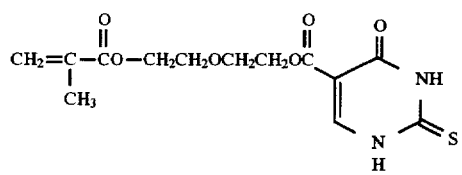

NMR (δ, ppm); 1.86 (3H, —CH$_3$),
3.70 (4H, —CH$_2$CH$_2$—O—CH$_2$CH$_2$—)
4.21, 4.26 (2H, 2H, —CH$_2$CH$_2$—O—CH$_2$CH$_2$—)
5.66, 6.01 (2H, CH$_2$=C—),
7.95 (1H, —N—CH=C—),
12.8 (2H, —NH—)
MASS (M+1)$^+$=329
Elementary analysis; C$_{13}$H$_{16}$N$_2$O$_6$S

|  | C | H | N |
|---|---|---|---|
| Calculated | 47.56 | 4.91 | 8.53 |
| Found | 47.37 | 4.84 | 8.41 |

EXAMPLE 10

Under an atmosphere of nitrogen, an acetonitrile solution (30 ml) of methacryloyl chloride (20.9 g, 0.2 mol) was slowly added dropwise at room temperature, using a dropping funnel, to 1,3-bis(3-hydroxypropyl)-1,1,3,3-tetramethyldisiloxane (100 g, 0.40 mol), molecular sieve 3A powder (40 9) and acetonitrile (470 ml) in a 1-L three-necked flask. After the completion of the dropwise addition, the mixture was refluxed with heating for 5 hours. The mixture was then left alone to cool to room temperature, the molecular sieve 3A powder was filtered out from the reaction mixture, and acetonitrile was distilled off under reduced pressure from the filtrate. Methylene chloride (300 ml) was added to the residue, and the resultant methylene chloride solution was washed with water. The methylene chloride layer was dried over anhydrous sodium sulfate, and the solvent was distilled off under reduced pressure. 1-(3-Methacryloyloxypropyl)-3-(3-hydroxypropyl)-1,1,3,3-tetramethyldisiloxane (46.2 g) was separated and purified as a colorless transparent liquid from this residue by silica gel column chromatography.

1-(3-Methacryloyloxypropyl)-3-(3-hydroxypropyl)-1,1,3,3-tetramethyldisiloxane (9.54 g, 30 mmol), N,N'-dicyclohexylcarbodiimide (2.27 g, 11 mmol), 5-carboxy-2-thiouracil (1.72 g, 10 mmol) and tetrahydrofuran (50 ml) were put in a 200-ml three-necked flask to make a solution, and the solution was continuously stirred at room temperature for 3 days. A white precipitate was formed as the reaction progressed, and after the completion of the reaction, the white precipitate was filtered out. Then, the same separation and purification operations as in Example 1 were carried out to give Compound [J] represented by the following formula. The results of NMR (d6DMSO), MASS and elementary analysis are shown below.

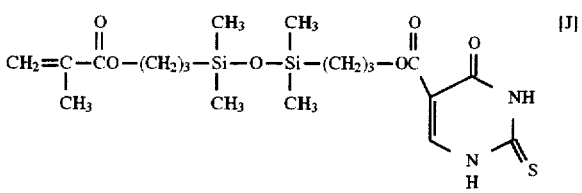

NMR (δ, ppm); 0.06 (12H,—Si—CH$_3$),
0.51 (4H, —Si—CH$_2$—CH$_2$—CH$_2$—OCO—),
1.69 (4H, —Si—CH$_2$—CH$_2$—CH$_2$—OCO—),
1.87 (3H, —CH$_3$),
4.23 (4H, —Si—CH$_2$—CH$_2$—CH$_2$—OCO—),
5.67, 6.03 (2H, CH$_2$=C—),
7.96 (1H, —N—CH=C—),
12.8 (2H, —NH—)
MASS (M+1)$^+$=473
Elementary analysis; C$_{19}$H$_{32}$N$_2$O$_6$SSi$_2$

|  | C | H | N |
|---|---|---|---|
| Calculated | 48.28 | 6.82 | 5.93 |
| Found | 48.35 | 6.74 | 5.73 |

EXAMPLE 11

Under an atmosphere of nitrogen, an ethanol solution (100 ml) of diethyl ethoxymethylenemalonate (43.2 g, 0.2 mol) was slowly added dropwise at room temperature, using a dropping funnel, to an ethanol solution (200 ml) of sodium ethoxide (13.6 g, 0.20 mol) in a 1-L three-necked flask. After the completion of the dropwise addition, the mixture was refluxed with heating. Successively, an ethanol solution (100 ml) of methylthiourea (18.0 g, 0.2 mol) was slowly added dropwise using a dropping funnel. After the completion of the dropwise addition, the mixture was refluxed with heating for 3 hours. Then, the reaction mixture was left alone to cool to room temperature, and added to water (500 ml) in a beaker. Concentrated hydrochrolic acid was added to the resultant solution, then light yellow solid was formed. Then the solid was filtered out, and, ethyl 3-methyl-2-thiouracil-5-carboxylate(14.1 g) was separated and purified by column chromatography.

Potassium tertiary butoxide (43.7 g, 389 mmol) and dimethyl sulfoxide (400 ml) were put in a 2-L egg-plant type flask to make a solution, and ethyl 3-methyl-2-thiouracil-5-carboxylate (5.35 g, 25.0 mmol) was slowly added dropwise to the solution, and the mixture was subjected to reaction at room temperature for 1 hour. After the completion of the reaction, methanol (500 ml) was added to the reaction mixture, and the precipitate deposited was filtered out. The resultant precipitate was dissolved in water, and hydrochloric acid was added to this aqueous to give 5-carboxy-3-methyl-2-thiouracil (2.88 g) as a light yellow solid.

6-Hydroxyhexyl methacrylate (5.59 g, 30.0 mmol), N,N'-dicyclohexylcarbodiimide (2.27 g, 11 mmol), 5-carboxy-3-methyl-2-thiouracil (1.86 g, 10 mmol) and tetrahydrofuran (50 ml) were put in a 200-ml three-necked flask to make a solution, and the solution was continuously stirred at room temperature for 3 days. A white precipitate was formed as the reaction progressed, and after the completion of the reaction, the white precipitate was filtered out. Then, the same separation and purification operations as in Example 1 were carried out to give 6-methacryloyloxyhexyl 3-methyl-2-thiouracil-5-carboxylate |K| (1.16 g, 3.28 mmol) represented by the following formula. The results of NMR (d6DMSO), MASS and elementary analysis are shown below.

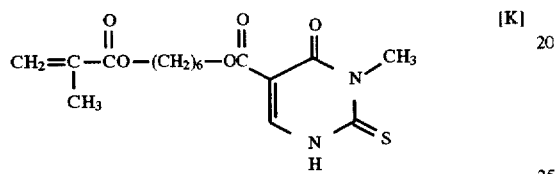

NMR (δ, ppm); 1.3-1.7 (8H, —COO—CH$_2$(CH$_2$)$_4$CH$_2$—OCO—)
1.87 (3H, —CH$_3$)
3.78 (3H, N—CH$_3$)
4.09, 4.13 (4H, —COO—CH$_2$(CH$_2$)$_4$CH$_2$—OCO—)
5.65, 6.01 (2H, CH$_2$=C—)
7.94 (1H, —N—CH=C—)
12.4 (1H, —NH—)
MASS (M+1)$^+$=354
Elementary analysis; C$_{16}$H$_{22}$N$_2$O$_5$S

|  | C | H | N |
|---|---|---|---|
| Calculated | 54.22 | 6.25 | 7.90 |
| Found | 54.20 | 6.23 | 7.93 |

EXAMPLE 12

Ethyl 1-methyl-2-thiouracil-5-carboxylate (15.3 g), an isomer of ethyl 3-methyl-2-thiouracil-5-carboxylate prepared in Example 8, was obtained as they were purified.

Potassium tertiary butoxide (43.7 g, 389 mmol) and dimethyl sulfoxide (400 ml) were put in a 2-L egg-plant type flask to make a solution, and ethyl 1-methyl-2-thiouracil-5-carboxylate (5.3 g, 25.0 mmol) was slowly added dropwise to the solution, and the mixture was subjected to reaction at room temperature for 1 hour. After the completion of the reaction, methanol (500 ml) was added to the reaction mixture, and the precipitate deposited was filtered out. The resultant precipitate was dissolved in water, and hydrochloric acid was added to this solution to give 5-carboxy-1-methyl-2-thiouracil (2.65 g) as a light yellow solid.

6-Hydroxyhexyl methacrylate (5.59 g, 30.0 mmol), N,N'-dicyclohexylcarbodiimide (2.27 g, 11 mmol), 5-carboxy-1-methyl-2-thiouracil (1.86 g, 10 mmol) and tetrahydrofuran (50 ml) were put in a 200-ml three-necked flask to make a solution, and the solution was continuously stirred at room temperature for 3 days. A white precipitate was formed as the reaction progressed, and after the completion of the reaction, the white precipitate was filtered out. Then, the same separation and purification operations as in Example 1 were carried out to give 6-methacryloyloxyhexyl 1-methyl-2-thiouracil-5-carboxylate |L| (1.23 g, 3.56 mmol) represented by the following formula. The results of NMR (d6DMSO), MASS and elementary analysis are shown below.

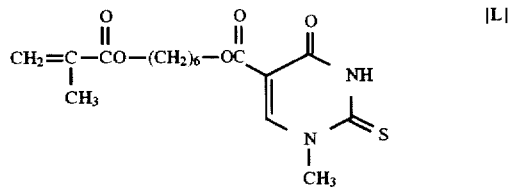

NMR (δ, ppm); 1.3-1.7 (8H, —COO—CH$_2$(CH$_2$)$_4$CH$_2$—OCO—)
1.87 (3H, —CH$_3$)
3.61 (3H, N—CH$_3$)
4.09, 4.13 (4H, —COO—CH$_2$(CH$_2$)$_4$CH$_2$—OCO—)
5.65, 6.01 (2H, CH$_2$=C—)
7.94 (1H, —N—CH=C—)
12.4 (1H, —NH—)
MASS (M+1)$^+$=354
Elementary analysis; C$_{16}$H$_{22}$N$_2$O$_5$S

|  | C | H | N |
|---|---|---|---|
| Calculated | 54.22 | 6.26 | 7.90 |
| Found | 54.21 | 6.24 | 7.90 |

EXAMPLE 13

Under an atmosphere of nitrogen, an ethanol solution (50 ml) of diethyl malonate (16.0 g, 0.1 mol) was slowly added dropwise at room temperature, using a dropping funnel, to an ethanol solution (200 ml) of sodium ethoxide (13.6 g, 0.2 mol) in a 1-L three-necked flask. After the completion of the dropwise addition, the mixture was refluxed with heating. Successively, an ethanol solution (100 ml) of triethyl orthobenzoate (22.4 g, 0.1 mol) was slowly added dropwise, using a dropping funnel. After the completion of the dropwise addition, the mixture was refluxed with heating for 6 hours. Then the reaction mixture was left alone to cool to room temperature, and ethanol was distilled off under reduced pressure. Water (200 ml) was added to the residue, and the mixture was extracted with ether (3 three times). The ether layer was washed with saturated sodium saline water, dried over anhydrous magnesium sulfate and concentrated. Then the residue was distilled off under reduced pressure. Diethyl 1'-ethoxy-1'-phenylmethylenemalonate (18.2 g) was obtained.

Under an atmosphere of nitrogen, an ethanol solution (50 ml) of diethyl 1'-ethoxy-1'-phenylmethylenemanlonate (14.6 g, 0.05 mol) was slowly added dropwise at room temperature, using a dropping funnel, to an ethanol solution (50 ml) of sodium ethoxide (3.4 g, 0.05 mol) in a 500 ml three-necked flask. After the completion of the dropwise addition, the mixture was refluxed with heating. Then, an ethanol solution (50 ml) of thiourea (3.8 g, 0.05 mol) was slowly added dropwise at room temperature using a dropping funnel. After the completion of the dropwise addition, the mixture was refluxed with heating for 3 hours. Then the reaction mixture was left alone to cool to room temperature, and reaction mixture was added to water (200 ml) in a beaker. Concentrated hydrochrolic acid was added to the resultant solution, then light yellow solid was formed. By filtration of the deposited solid, ethyl 6-phenyl-2-thiouracil-5-carboxylate (7.6 g) was obtained.

Potassium tertiary butoxide (43.7 g, 389 mmol) and dimethyl sulfoxide (400 ml) were put in a 2-L egg-plant type flask to make a solution, and ethyl 6-phenyl-2-thiouracil-5-carboxylate (6.90 g, 25.0 mmol) was slowly added dropwise to the solution, and the mixture was subjected to reaction at room temperature for 1 hour. After the completion of the reaction, methanol (500 ml) was added to the reaction mixture, and the precipitate deposited was filtered out. The resultant precipitate was dissolved in water, and hydrochloric acid was added to this aqueous solution to give 5-carboxy-6-phenyl-2-thiouracil (3.10 g) as a light yellow solid.

6-Hydroxyhexyl methacrylate (5.59 g, 30.0 mmol), N,N'-dicyclohexylcarbodiimide (2.27 g, 11 mmol), 5-carboxy-6-phenyl-2-thiouracil (2.00 g, 10 mmol) and tetrahydrofuran (50 ml) were put in a 200-ml three-necked flask to make a solution, and the solution was continuously stirred at room temperature for 3 days. A white precipitate was formed as the reaction progressed, and after the completion of the reaction, the white precipitate was filtered out. Then, the same separation and purification operations as in Example 1 were carried out to give 6-methacryloyloxyhexyl 6-phenyl-2-thiouracil-5-carboxylate [M] (1.29 g, 3.10 mmol) represented by the following formula. The results of NMR (d6DMSO), MASS and elementary analysis are shown below.

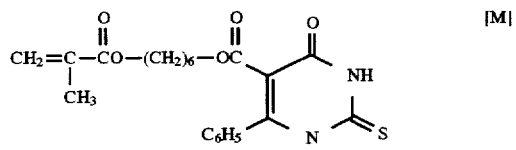

[M]

NMR (δ, ppm); 1.3–1.7 (8H, —COO—CH$_2$ (CH$_2$)$_4$CH$_2$—OCO—)

1.87 (3H, C=C—CH$_3$ )

4.09, 4.13 (4H, —COO—CH$_2$(CH$_2$)$_4$CH$_2$—OCO—)

5.65, 6.01 (2H, CH$_2$=C—)

7.62 (5H, C$_6$H$_5$)

12.5 (2H, —NH—)

MASS (M+1)$^+$=416

Elementary analysis; C$_{21}$H$_{24}$N$_2$O$_5$S

|  | C | H | N |
|---|---|---|---|
| Calculated | 60.56 | 5.81 | 6.73 |
| Found | 60.55 | 5.79 | 6.73 |

EXAMPLE 14

Under an atmosphere of nitrogen, an ethanol solution (100 ml) of diethyl 2-oxosuccinate (37.6 g, 0.20 mol) was slowly added dropwise at room temperature, using a dropping funnel, to ethanol solution (200 ml) of sodium ethoxide (13.6 g, 0.20 g) in a 1-L three-necked flask. After the completion of the dropwise addition, the mixture was refluxed with heating. Successively, an ethanol solution (100 ml) of thiourea (15.2 g, 0.20 mol) was slowly added dropwise at room temperature, using a dropping funnel. After the completion of the dropwise addition, the mixture was refluxed with heating for three hours. Then, the reaction mixture was left alone to cool to room temperature, and then the reaction mixture was added to water (500 ml) in a beaker. Concentrated hydrochloric acid was added to the resultant solution, then light yellow solid was formed. By filtration of the deposited solid, ethyl 2-thiouracil-6-carboxylate (28.4 g) was obtained.

Potassium tertiary butoxide (43.7 g, 389 mmol) and dimethyl sulfoxide (400 ml) were put in a 2-L egg-plant type flask to make a solution, ethyl 2-thiouracil-6-carboxylate (5.00 g, 25.0 mmol) was slowly added dropwise to the solution, and the mixture was subjected to reaction at room temperature for 1 hour. After the completion of the reaction, methanol (500 ml) was added to the reaction mixture, and the precipitate deposited was filtered out. The resultant precipitate was dissolved in water, and hydrochloric acid was added to this solution to give 6-carboxy-2-thiouracil (2.80 g) as a light yellow solid.

6-Hydroxyhexyl methacrylate (5.59 g, 30.0 mmol), N,N'-dicyclohexylcarbodiimide (2.27 g, 11 mmol), 6-carboxy-2-thiouracil (1.72 g, 10 mmol) and tetrahydrofuran (50 ml) were put in a 200-ml three-necked flask to make a solution, and the solution was continuously stirred at room temperature for 3 days. A white precipitate was formed as the reaction progressed, and after the completion of the reaction, the white precipitate was filtered out. Then, the same separation and purification operations as in Example 1 were carried out to give 6-methacryloyloxyhexyl 2-thiouracil-6-carboxylate [N] (1.07 g, 3.15 mmol) represented by the following formula. The results of NMR (d6DMSO), MASS and elementary analysis are shown below.

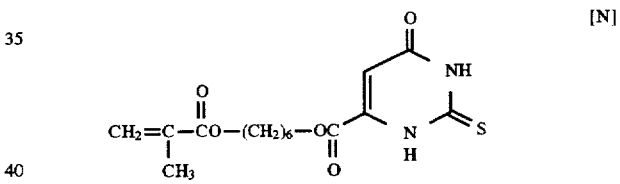

[N]

NMR (δ, ppm); 1.3–1.7 (8H, —COO—CH$_2$(CH$_2$)$_4$CH$_2$—OCO—)

1.87 (3H, —CH$_3$)

4.09, 4.13 (4H, —COO—CH$_2$(CH$_2$)$_4$CH$_2$—OCO—)

5.65, 6.01 (2H, CH$_2$=C—)

6.87 (1H, —N—CH=C—)

12.9 (2H, —NH—)

MASS (M+1)$^+$=340

Elementary analysis; C$_{15}$H$_{20}$N$_2$O$_5$S

|  | C | H | N |
|---|---|---|---|
| Calculated | 52.93 | 5.92 | 8.23 |
| Found | 52.96 | 5.95 | 8.25 |

EXAMPLE 15

Under an atmosphere of nitrogen, an ethanol solution (100 ml) of diethyl 2-methyl-2'-oxosuccinate (40.4 g, 0.20 mol) was slowly added dropwise at room temperature, using a dropping funnel, to an ethanol solution (200 ml) of sodium ethoxide (13.6 g, 0.20 mol) in a 1-L three-necked flask. After the completion of the dropwise addition, the mixture was refluxed with heating. Successively, an ethanol solution (100 ml) of thiourea (15.2 g, 0.20 mol) was slowly added dropwise at room temperature, using a dropping funnel. After the completion of the dropwise addition, the mixture was refluxed with heating for three hours. Then, the reaction mixture was left alone to cool to room temperature, and then the reaction mixture was added to water (500 ml) in a beaker. Concentrated hydrochloric acid was added to the resultant solution, then light yellow solid was formed. By filtration of the deposited solid, ethyl 5-methyl-2-thiouracil-6-carboxylate (26.5 g) was obtained.

Potassium tertiary butoxide (43.7 g, 389 mmol) and dimethyl sulfoxide (400 ml) were put in a 2-L egg-plant type flask to make a solution, ethyl 5-methyl-2-thiouracil-6-carboxylate (5.35 g, 25.0 mmol) was slowly added dropwise to the solution, and the mixture was subjected to reaction at room temperature for 1 hour. After the completion of the reaction, methanol (500 ml) was added to the reaction mixture, and the precipitate deposited was filtered out. The resultant precipitate was dissolved in water, and hydrochloric acid was added to this solution to give 6-carboxy-5-methyl-2-thiouracil (2.93 g) as a light yellow solid.

6-Hydroxyhexyl methacrylate (5.59 g, 30.0 mmol), N,N'-dicyclohexylcarbodiimide (2.27 g, 11 mmol), 6-carboxy-5-methyl-2-thiouracil (1.86 g, 10 mmol) and tetrahydrofuran (50 ml) were put in a 200-ml three-necked flask to make a solution, and the solution was continuously stirred at room temperature for 3 days. A white precipitate was formed as the reaction progressed, and after the completion of the reaction, the white precipitate was filtered out. Then, the same separation and purification operations as in Example 1 were carried out to give 6-methacryloyloxyhexyl 5-methyl-2-thiouracil-6-carboxylate [O] (1.13 g, 3.19 mmol) represented by the following formula. The results of NMR (d6DMSO), MASS and elementary analysis are shown below.

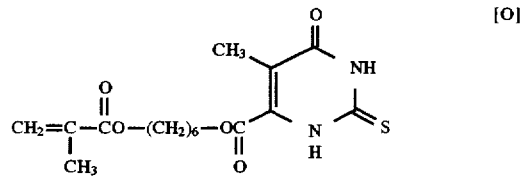

[O]

NMR (δ, ppm): 1.3–1.7 (8H, —COO—CH$_2$(CH$_2$)$_4$CH$_2$—OCO—)
1.87 (3H, CH$_2$=C—CH$_3$)
2.34 (3H, C=C—CH$_3$ )
4.09, 4.13 (4H, —COO—CH$_2$(CH$_2$)$_4$CH$_2$—OCO—)
5.65, 6.01 (2H, CH$_2$=C—)
12.6 (2H, —NH—)
MASS (M+1)$^+$=354
Elementary analysis: C$_{16}$H$_{22}$N$_2$O$_5$S

|  | C | H | N |
|---|---|---|---|
| Calculated | 54.22 | 6.25 | 7.90 |
| Found | 54.19 | 6.23 | 7.90 |

EXAMPLE 16

Under an atmosphere of nitrogen, an ethanol solution (100 ml) of diethyl 2-methyl-2'-oxosuccinate (40.4 g, 0.20 mol) was slowly added dropwise at room temperature, using a dropping funnel, to an ethanol solution (200 ml) of sodium ethoxide (13.6 g, 0.20 g) in a 1-L three-necked flask. After the completion of the dropwise addition, the mixture was refluxed with heating. Successively, an ethanol solution (100 ml) of methylthiourea (18.0 g, 0.20 mol) was slowly added dropwise at room temperature, using a dropping funnel. After the completion of the dropwise addition, the mixture was refluxed with heating for three hours. Then, the reaction mixture was left alone to cool to room temperature, and then the reaction mixture was added to water (500 ml ) in a beaker. Concentrated hydrochloric acid was added to the resultant solution, then light yellow solid was formed. The solid deposited was filtered out then ethyl 3,5-dimethyl-2-thiouracil-6-carboxylate (16.2 g) was separated and purified by column chromatography.

Potassium tertiary butoxide (43.7 g, 389 mmol) and dimethyl sulfoxide (400 ml) were put in a 2-L egg-plant type flask to make a solution, ethyl 3,5-dimethyl-2-thiouracil-6-carboxylate (5.70 g, 25.0 mmol) was slowly added dropwise to the solution, and the mixture was subjected to reaction at room temperature for 1 hour. After the completion of the reaction, methanol (500 ml) was added to the reaction mixture, and the precipitate deposited was filtered. The resultant precipitate was dissolved in water, and hydrochloric acid was added to this solution to give 6-carboxy 3,5-dimethyl-2-thiouracil (2.88 g) as a light yellow solid.

6-Hydroxyhexyl methacrylate (5.59 g, 30 mmol), N,N'-dicyclohexylcarbodiimide (2.27 g, 11 mmol), 6-carboxy-3,5-dimethyl-2-thiouracil (2.00 g, 10 mmol) and tetrahydrofuran (50 ml) were put in a 200-ml three-necked flask to make a solution, and the solution was continuously stirred at room temperature for 3 days. A white precipitate was formed as the reaction progressed, and after the completion of the reaction, the white precipitate was filtered out. Then, the same separation and purification operations as in Example 1 were carried out to give 6-methacryloyloxyhexyl 3,5-dimethyl- 2-thiouracil-6-carboxylate [P] (1.13 g, 3.07 mmol) represented by the following formula. The results of NMR (d6DMSO), MASS and elementary analysis are shown below.

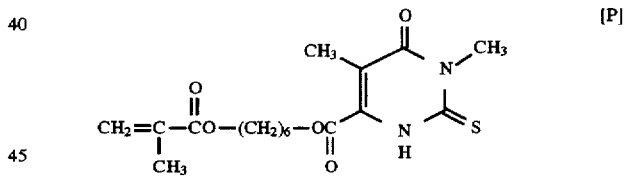

[P]

NMR (δ, ppm): 1.3–1.7 (8H, —COO—CH$_2$(CH$_2$)$_4$CH$_2$—OCO—)
1.87 (3H, CH$_2$=C—CH$_3$)
2.36 (3H, C=C—CH$_3$)
3.68 (3H, N—CH$_3$)
4.09, 4.13 (4H, —COO—CH$_2$(CH$_2$)$_4$CH$_2$—OCO—)
5.65, 6.01 (2H, CH$_2$=C—)
12.3 (1H, —NH—)
MASS (M+1)$^+$=368
Elementary analysis: C$_{17}$H$_{24}$N$_2$O$_5$S

|  | C | H | N |
|---|---|---|---|
| Calculated | 55.42 | 6.57 | 7.60 |
| Found | 55.48 | 6.54 | 7.61 |

EXAMPLE 17

Under an atmosphere of nitrogen, an ethanol solution (50 ml) of diethyl malonate (16.0 g, 0.1 mol) was slowly added dropwise at room temperature, using a dropping funnel, to an ethanol solution (200 ml) of sodium ethoxide (13.6 g, 0.2 mol) in a 1-L three-necked flask. After the completion of the dropwise addition, the mixture was refluxed with heating. Successively, an ethanol solution (100 ml) of triethyl orthopropionate (17.6 g, 0.1 mol) was slowly added dropwise, using a dropping funnel. After the completion of the dropwise addition, the mixture was refluxed with heating for 6 hours. The mixture was then left alone to cool to room temperature, ethanol was distilled off under reduced pressure, 200 ml of water was added to the residue, and the mixture was extracted with ether (three times). The ether layer was washed with saturated aqueous sodium chloride solution, dried over anhydrous magnesium sulfate, and concentrated. The residue was distilled under reduced pressure to give diethyl 1-ethoxy-1-ethylmethylenemalonate (17.2 g).

Under an atmosphere of nitrogen, an ethanol solution (50 ml) of diethyl 1-ethoxy-1-ethylmethylenemalonate (12.2 g, 0.05 mol) was slowly added dropwise at room temperature, using a dropping funnel, to an ethanol solution (50 ml) of sodium ethoxide (3.4 g, 0.05 mol) in a 500-ml three-necked flask. After the completion of the dropwise addition, the mixture was refluxed with heating. Successively, an ethanol solution (50 ml) of thiourea (3.8 g, 0.05 mol) was slowly added dropwise at room temperature, using a dropping funnel. After the completion of the dropwise addition, the mixture was refluxed with heating for 3 hours. The mixture was then left alone to cool to room temperature, and the reaction mixture was added to water (200 ml) in a beaker. Concentrated hydrochloric acid was added to the resultant solution, and thereby a light yellow solid was deposited. The deposited solid was filtered to give ethyl 6-ethyl-2-thiouracil-5-carboxylate (7.3 g).

Potassium tertiary butoxide (43.7 g, 389 mol) and dimethyl sulfoxide (400 ml) were put in a 2-L egg-plant type flask to make a solution, ethyl 6-ethyl-2-thiouracil-5-carboxylate (5.70 g, 25.0 mol) was slowly added dropwise to this solution, and the mixture was subjected to reaction at room temperature for 1 hour. After the completion of the reaction, methanol (500 ml) was added to the reaction mixture, and the precipitate deposited was filtered. The obtained precipitate was dissolved in water, and hydrochloric acid was added to this aqueous solution to give 5-carboxy-6-ethyl-2-thiouracil (3.10 g) as a light yellow solid.

6-Hydroxyhexyl methacrylate (5.59 g, 30 mmol), N,N'-dicyclohexylcarbodiimide (2.27 g, 11 mmol), 5-carboxy-6-ethyl-2-thiouracil (2.00 g, 10 mmol) and tetrahydrofuran (50 ml) were put in a 200-ml three-necked flask to make a solution, and the solution was continuously stirred at room temperature for 3 days. A white precipitate was formed as the reaction progressed, and after the completion of the reaction, the white precipitate was filtered out. Then, the same separation and purification operations a in Example 1 were carried out to give 6-methacryloyloxyhexyl-6-ethyl-2-thiouracil-5-carboxylate [Q] (1.14 g, 3.1 mmol) represented by the following formula. The results of NMR (d6DMSO), MASS and elementary analysis are shown below.

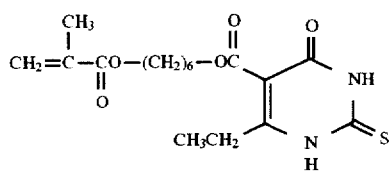

NMR (δ, ppm); 1.02 (3H, —CH$_2$CH$_3$)
1.3-1.7 (8H, —COO—CH$_2$(CH$_2$)$_4$CH$_2$—OCO—)
1.87 (3H, C=C—CH$_3$)
2.05 (2H, —CH$_2$CH$_3$)
4.09, 4.13 (4H, —COO—CH$_2$(CH$_2$)$_4$CH$_2$—OCO—)
5.65, 6.01 (2H, CH$_2$=C—)
12.5 (2H, —NH—)
MASS (M+1)$^+$=369
Elementary analysis; C$_{17}$H$_{24}$N$_2$O$_5$S

|  | C | H | N |
|---|---|---|---|
| Calculated | 55.42 | 6.57 | 7.60 |
| Found | 55.42 | 6.59 | 7.63 |

EXAMPLES 18 TO 34 AND COMPARATIVE EXAMPLES 1 to 4

17 Thiouracil derivatives (A to Q) shown in Table 1, and the following known 11-methacryloyloxy-1,1-undecanedicarboxylic acid [R], 10-methacryloyloxy-decyl dihydrogenphosphate [S] and 4-methacryloyloxyethyl trimellitate anhydride [T] were used, and the adhesive effects thereof on dental noble metals were examined, respectively. The structures and abbreviations of the thiouracil derivatives are as shown above.

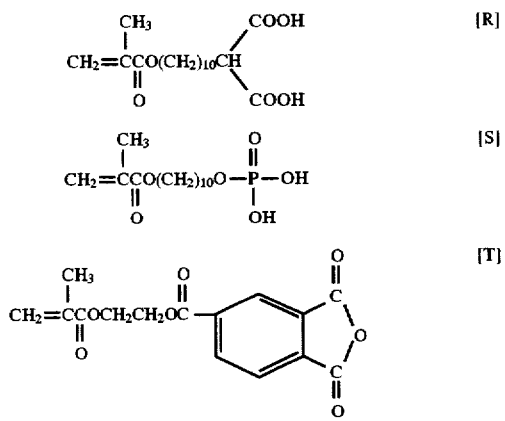

Each of these compounds is made to be an acetone solution of a concentration of 0.5% by weight which was assumed to be a metal surface-treating agent. "KINPARA 12", a dental gold-silver-palladium alloy (made by Towa Giken Co., 10×10×3 mm) and a pure gold plate (10×10×3 mm), which were adherends, were abraded with #1500 waterproof abrasive paper, and then sandblasted. An adhesive tape wherein a hole of 4 mm in diameter was made was stuck on the treated surface of each adherend to fix an area to be adhesive-treated. Each of the surfaces was coated with each of the previously prepared metal surface-treating agents, using a brush, respectively, and the acetone was volatilized by air drying. One minute later, kneaded paste of "Bistite resin cement" (made by Tokuyama), a dental adhesive, was piled on each of the surfaces treated with each of the metal surface-treating agents, respectively. Then, a 8 mm×18 mm SUS304-made round bar, which was previously sandblasted, was pressed on each of the adhesive surfaces to carry out adhesion, respectively. The excess resin cement was removed, and one hour later, each adhesion test piece was immersed in water of 37° C . 24 Hours later, tensile adhesive strength was measured, using an autograph (crosshead speed: 10 mm/min) made by SHIMADZU CORPORATION. In each case, the measured values on 6 test pieces were averaged, and the measurement results were shown in Table 1.

TABLE 1

|  |  | Adhesive component in the surface-treating agent | Adhesive strength to KINPARA 12 MPa | Adhesive strength to the pure gold plate MPa |
| --- | --- | --- | --- | --- |
| Example | 18 | A | 21 | 25 |
|  | 19 | B | 24 | 29 |
|  | 20 | C | 24 | 28 |
|  | 21 | D | 22 | 27 |
|  | 22 | E | 18 | 23 |
|  | 23 | F | 20 | 25 |
|  | 24 | G | 22 | 27 |
|  | 25 | H | 22 | 25 |
|  | 26 | I | 22 | 25 |
|  | 27 | J | 22 | 24 |
|  | 28 | K | 21 | 25 |
|  | 29 | L | 22 | 24 |
|  | 30 | M | 23 | 28 |
|  | 31 | N | 23 | 27 |
|  | 32 | O | 24 | 27 |
|  | 33 | P | 20 | 24 |
|  | 34 | Q | 23 | 28 |
| Comparative example | 1 | R | 11 | 10 |
|  | 2 | S | 10 | 9 |
|  | 3 | T | 10 | 9 |
|  | 4 | — | 10 | 9 |

EXAMPLES 35–43

Using Compound (B) shown in Example 19 in Table 1, the effect of the concentration of the adhesive component contained in the metal surface-treating agent was examined. Namely, Compound (B) was dissolved in acetone to prepare acetone solutions having concentrations of 10, 5, 1, 0.5, 0.1, 0.01, 0.005 and 0.001% by weight, respectively. The same operations as in Examples 18 to 34 were carried out except that each of these solutions was used as a metal surface-treating agent, and thereby adhesive effects on "KINPARA 12", a dental gold-silver-palladium alloy, and a pure gold plate were examined. The results are shown in Table 2.

TABLE 2

|  |  | Concentration of the adhesive component wt % | Adhesive strength to KINPARA 12 MPa | Adhesive strength to the pure gold plate MPa |
| --- | --- | --- | --- | --- |
| Example | 35 | 20.0 | 15 | 16 |
|  | 36 | 10.0 | 16 | 18 |
|  | 37 | 5.0 | 19 | 21 |
|  | 38 | 1.0 | 22 | 25 |
|  | 39 | 0.5 | 25 | 28 |
|  | 40 | 0.1 | 23 | 28 |
|  | 41 | 0.01 | 20 | 24 |
|  | 42 | 0.005 | 17 | 17 |
|  | 43 | 0.001 | 14 | 16 |

EXAMPLE 44 AND COMPARATIVE EXAMPLE 5

A 0.5% methyl methacrylate solution of Compound (B) used in Example 9 was prepared. In the same manner as in Examples 18 to 34, "KINPARA 12", a dental noble metal alloy, was coated with the solution, and one minute later, the coated surface was washed with pure acetone, and the same stainless steel bar as in the examples was bonded onto the coated surface with "Bistite resin cement" (made by Tokuyama) to prepare an adhesion test piece (Example 44). On the other hand, a test piece coated with methyl methacrylate alone (Comparative example 5) was also prepared as a comparative example. In the same manner as in Examples 18 to 34, these test pieces were immersed in water of 37° C. for one day, and tensile adhesive strength was measured. As a result, the average adhesive strength was 23 MPa in Example 44, whereas 10 MPa in Comparative example 5.

EXAMPLES 45 TO 61 AND COMPARATIVE EXAMPLE 6

A 0.5% acetone solution of Compound A used in Example 18 was prepared. In the same manner as in Examples 18 to 34, "KINPARA 12", a dental noble metal alloy, and a "pure gold plate" were coated with the solution, and after the adherends were air dried, the same stainless steel bar as in Examples 18 to 34 was bonded onto the adherends with "Bistite resin cement" (made by Tokuyama) to prepare adhesion test pieces (Example 45). Likewise, adhesion test pieces (Examples 46 to 61) were prepared using Compounds B to Q. On the other hand, the same stainless steel bar as in Examples 18 to 34 was bonded, using Bistite resin cement, onto "KINPARA 12" and a "pure gold plate" each coated with pure acetone liquid alone, to prepare test pieces (Comparative example 6). For the assessment of adhesion durability, one hour after the adhesion, these test pieces were immersed in water of 37° C., and 24 hours later, a heat cycle test wherein the test pieces were alternately immersed in temperature-adjustable water baths, each kept at 4° C. and 60° C., each for one minute was carried out 5,000 times, and then tensile adhesive strength was measured. The results are shown in Table 3.

TABLE 3

|  |  | Adhesive component in the surface-treating agent | Adhesive strength to KINPARA 12 MPa | Adhesive strength to the pure gold plate MPa |
| --- | --- | --- | --- | --- |
| Example | 45 | A | 17 (21) | 19 (25) |
|  | 46 | B | 22 (24) | 26 (29) |
|  | 47 | C | 21 (24) | 26 (28) |
|  | 48 | D | 20 (22) | 24 (27) |
|  | 49 | E | 16 (18) | 20 (23) |
|  | 50 | F | 17 (20) | 20 (25) |
|  | 51 | G | 20 (22) | 23 (27) |
|  | 52 | H | 21 (22) | 23 (25) |
|  | 53 | I | 22 (22) | 24 (25) |
|  | 54 | J | 22 (22) | 23 (24) |
|  | 55 | K | 21 (21) | 23 (25) |
|  | 56 | L | 20 (22) | 23 (24) |
|  | 57 | M | 21 (23) | 25 (28) |
|  | 58 | N | 20 (23) | 24 (27) |
|  | 59 | O | 23 (24) | 25 (27) |

TABLE 3-continued

|  |  | Adhesive component in the surface-treating agent | Adhesive strength to KINPARA 12 MPa | Adhesive strength to the pure gold plate MPa |
|---|---|---|---|---|
|  | 60 | P | 20 (20) | 24 (24) |
|  | 61 | Q | 21 (23) | 25 (28) |
| Comparative example | 6 | — | 2 (10) | 2 (9) |

( ) Initial adhesive strength

Whenever any of the metal surface-treating agents was used (Examples 45 to 61), there was no case where the adhesive strength of each metal after the heat cycle test was largely lowered compared with the initial adhesive strength (the values in the parentheses in Table 3). On the other hand, in Comparative example 6, the adhesive strength was largely lowered.

EXAMPLES 62 TO 78

A 0.5% acetone solution of Compound A used in Example 18 was prepared, and then in order to assess the storage stability of the primer, the solution was stored in a constant temperature chamber of 37° C. for 2 months. In the same manner as in Examples 18 to 34, "KINPARA 12", a dental noble metal alloy, and a "pure gold plate" were coated with the primer after the storage, and after the adherends were air dried, the same stainless steel bar as in Examples 18 to 34 was bonded onto the adherends with "Bistite resin cement" (made by Tokuyama) to prepare adhesion test pieces (Example 62). Likewise, 0.5% acetone solutions of Compounds B to Q were prepared, and stored at 37° C. for 2 months, adhesion was carried out using them to give adhesion test pieces (Examples 63 to 78). One hour after the adhesion, these test pieces were immersed in water of 37° C., and 24 hours later, tensile adhesive strength was measured. The results are shown in Table 4.

TABLE 4

|  |  | Adhesive component in the surface-treating agent | Adhesive strength to KINPARA 12 MPa | Adhesive strength to the pure gold plate MPa |
|---|---|---|---|---|
| Example | 62 | A | 20 (21) | 23 (25) |
|  | 63 | B | 25 (24) | 29 (29) |
|  | 64 | C | 24 (24) | 28 (28) |
|  | 65 | D | 22 (22) | 26 (27) |
|  | 66 | E | 19 (18) | 22 (23) |
|  | 67 | F | 18 (20) | 26 (25) |
|  | 68 | G | 23 (22) | 27 (27) |
|  | 69 | H | 22 (22) | 24 (25) |
|  | 70 | I | 23 (22) | 25 (25) |
|  | 71 | J | 21 (22) | 22 (24) |
|  | 72 | K | 20 (21) | 23 (25) |
|  | 73 | L | 23 (22) | 24 (24) |
|  | 74 | M | 22 (23) | 25 (28) |
|  | 75 | N | 25 (23) | 26 (27) |
|  | 76 | O | 23 (24) | 25 (27) |
|  | 77 | P | 20 (20) | 25 (24) |
|  | 78 | Q | 22 (23) | 25 (28) |

( ) Initial adhesive strength

Also when the metal surface-treating agents after the storage at 37° C. for 2 months were used (Examples 62 to 78), there was no case where the adhesive strength to each metal was largely lowered compared with the initial adhesive strength (the values in the parentheses in Table 4).

EXAMPLE 79

10-Methacryloyloxydecyl 2-thiouracil-5-carboxylate [C] (0.001 g), 11-methacryloyloxy-1,1-undecane-dicarboxylic acid [R] (1.4 g) and acetone (18.599 g) were mixed to give a uniform solution, which was assumed to be a metal surface-treating agent. "KINPARA 12", a dental gold-silver-palladium alloy (made by Towa Giken Co., 10×10×3 mm), "WACROME", a dental cobalt-chromium alloy (made by Towa Giken Co., 10×10×3 mm), a pure gold plate (10×10×3 mm) and a pure copper plate (10×10×3 mm) which were adherends, were abraded with #1500 waterproof abrasive paper, and then sandblasted. An adhesive tape wherein a hole of 4 mm in diameter was made was stuck on the treated surface of each adherend to fix an area to be adhesive-treated. Each of the surfaces was coated with the previously prepared metal surface-treating agent, using a brush, and the acetone was volatilized by air drying. One minute later, kneaded paste of "Bistite resin cement" (made by Tokuyama), a dental adhesive, was piled on each of the surfaces treated with the metal surface-treating agent. Then, a 8 mm×18 mm SUS304-made round bar, which was previously sandblasted, was pressed on each of the adhesive surfaces to carry out adhesion, respectively. The excess resin cement was removed, and one hour later, each adhesion test piece was immersed in water of 37° C. 24 Hours later, tensile adhesive strength was measured, using an autograph (crosshead speed: 10 mm/min) made by SHIMADZU CORPORATION. In each case, the measured values on 6 test pieces were averaged, and the measurement results were shown in Table 6.

EXAMPLES 80 TO 93

Metal surface-treating agents of the compositions shown in Table 5 were prepared according to the process of Example 79, and adhesive strength to various metals were measured in the same manner as therein. The measurement results are shown in Table 6. In this connection, the structures and abbreviations of the acidic group-containing (meth)acrylate monomers used are shown below.

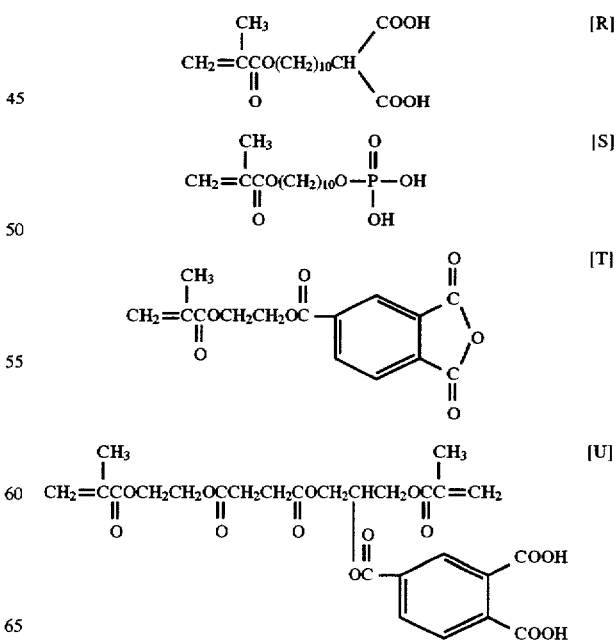

-continued

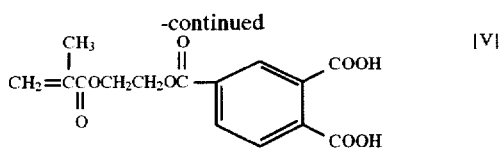
[V]

TABLE 5

|  | Thiouracil derivative (wt %) | | Acidic group-containing (meth)acrylate monomer (wt %) | | Organic solvent |
|---|---|---|---|---|---|
| Example 79 | C | 0.005 | R | 7 | acetone |
| Example 80 | P | 0.05 | R | 0.1 | acetone |
| Example 81 | B | 0.05 | U | 5 | acetone |
| Example 82 | D | 0.1 | S | 3 | acetone |
| Example 83 | H | 0.1 | R | 5 | acetone |
| Example 84 | B | 0.1 | R | 10 | ethanol |
| Example 85 | Q | 0.2 | U + R = 3 + 4 | | acetone |
| Example 86 | C | 0.2 | R | 5 | ethanol |
| Example 87 | C | 0.5 | T | 10 | acetone |
| Example 88 | F | 0.5 | U | 15 | acetone/toluene = 1/1 |
| Example 89 | B | 0.5 | R | 5 | acetone |
| Example 90 | B | 1.0 | V | 5 | MMA |
| Example 91 | J | 1.0 | R | 5 | acetone |
| Example 92 | E | 5.0 | R | 3 | acetone |
| Example 93 | C | 10.0 | U | 7 | toluene |

TABLE 6

|  | KINPARA 12 MPa | Pure gold plate MPa | WACROME MPa | Pure copper plate MPa |
|---|---|---|---|---|
| Example 79 | 20 | 17 | 33 | 26 |
| Example 80 | 21 | 23 | 26 | 21 |
| Example 81 | 25 | 26 | 33 | 25 |
| Example 82 | 24 | 26 | 33 | 24 |
| Example 83 | 24 | 24 | 33 | 24 |
| Example 84 | 27 | 28 | 34 | 26 |
| Example 85 | 27 | 27 | 35 | 27 |
| Example 86 | 28 | 27 | 35 | 26 |
| Example 87 | 28 | 28 | 34 | 25 |
| Example 88 | 23 | 24 | 28 | 22 |
| Example 89 | 29 | 28 | 35 | 27 |
| Example 90 | 27 | 26 | 33 | 25 |
| Example 91 | 23 | 24 | 33 | 23 |
| Example 92 | 20 | 19 | 32 | 24 |
| Example 93 | 18 | 19 | 33 | 25 |

Examples 81, 82, 84, 87 and 90 represent the results in the cases where different acidic group-containing (meth)acrylate monomers were used. Examples 80, 82, 83, 85, 86, 88, 89, 91 and 92 represent the results in the cases where different thiouracil derivatives were used, and Examples 84, 87, 90 and 93 represent the results in the cases where different solvents were used. Examples 79 and 93 show the range of the content of the thiouracil derivative on which the test was carried out, and Examples 80 and 88 show the range of the content of the acidic group-containing (meth)acrylate monomer on which the test was carried out. Example 88 is an example wherein plural organic solvents were used, and Example 85 is an example wherein plural acidic group-containing (meth)acrylate monomers were used. In all the examples, adhesive strength to "KINPARA 12", "WACROME", the pure gold plate and the pure copper plate were good.

Further, as apparent from comparison between Example 87 and Example 20 and between Example 89 and Example 19, the adhesive strength to "KINPARA 12", an alloy composed of base metals and noble metals is higher, compared with the cases where an acidic group-containing (meth)acrylate monomer was not compounded.

EXAMPLES 94 TO 95 AND COMPARATIVE EXAMPLES 7 to 8

In the same manner as in Example 79, metal surface-treating agents of the compositions shown in Table 7 were prepared and assessment was made. The results are shown in Table 8.

TABLE 7

|  | Thiouracil derivative (wt %) | | Acidic group-containing (meth)acrylate monomer (wt %) | | Organic solvent |
|---|---|---|---|---|---|
| Example 94 | B | 0.5 | — | | acetone |
| Example 95 | B | 0.5 | R | 20 | acetone |
| Comparative example 7 | — | | R | 5 | acetone |
| Comparative example 8 | B | 0.5 | R | 5 | — |

TABLE 8

|  | KINPARA 12 MPa | Pure gold plate MPa | WACROME MPa | Pure copper plate MPa |
|---|---|---|---|---|
| Example 94 | 23 | 29 | 24 | 19 |
| Example 95 | 22 | 23 | 25 | 18 |
| Comparative example 7 | 10 | 9 | 33 | 25 |
| Comparative example 8 | — | — | — | — |

Comparative example 7 is an example wherein a thiouracil derivative is not contained, and there arised problems in adhesive strength to "KINPARA 12" and the pure gold plate. In each of Examples 94 and 95, the content of the acidic group-containing (meth)acrylate monomer is out of the range, and therefore, the adhesive strength to "WACROME" and the pure copper plate is lowered. In Comparative example 8, an organic solvent is not contained, and therefore, the thiouracil derivative did not dissolve in the acidic group-containing (meth)acrylate monomer and a uniform solution was not obtained.

EXAMPLES 96 TO 102 AND COMPARATIVE EXAMPLE 9

"KINPARA 12" and "WACROME" as dental alloys, and a pure gold plate and a pure copper plate were coated with the metal surface-treating agent used in Example 89, according to the process of Example 79, and after the adherends were dried, the stainless steel bar was bonded to each of the surfaces of the adherends using "Bistite resin cement" (made by Tokuyama), whereby adhesion test pieces (Example 96) were obtained. Likewise, adhesion test pieces (Examples 97 to 102) were prepared using the metal surface-treating agents used in Examples 82, 83, 84, 85, 86 and 87. On the other hand, adhesion test pieces in the case where pure acetone liquid alone was applied (Comparative example 9) was also prepared. For the assessment of adhesion durabilities of these test pieces, one hour after the adhesion, these test pieces were immersed in water of 37° C., and 24 hours later, a heat cycle test wherein the test pieces were alternately immersed in temperature-adjustable water baths, each kept at 4° C. and 60° C., each for one minute was carried out 5,000 times, and then tensile adhesive strength was measured. The results are shown in Table 9.

TABLE 9

| | KINPARA 12 MPa | Pure gold plate MPa | WACROME MPa | Pure copper plate MPa |
|---|---|---|---|---|
| Example 96 | 28 (29) | 26 (28) | 33 (35) | 24 (27) |
| Example 97 | 21 (24) | 23 (26) | 31 (33) | 23 (24) |
| Example 98 | 23 (24) | 24 (24) | 31 (33) | 23 (24) |
| Example 99 | 25 (27) | 27 (28) | 31 (34) | 24 (26) |
| Example 100 | 24 (27) | 25 (27) | 32 (35) | 23 (27) |
| Example 101 | 28 (28) | 26 (27) | 31 (35) | 23 (26) |
| Example 102 | 25 (28) | 27 (28) | 34 (34) | 23 (25) |
| Comparative example 9 | 4 (10) | 3 (9) | 10 (23) | 9 (18) |

( ) Initial adhesive strength

Whenever any of the metal surface-treating agents was used (Examples 96 to 102), there was no case where the adhesive strength of each metal after the heat cycle test was largely lowered compared with the initial adhesive strength (the values in ( ) in Table 9). On the other hand, in Comparative example 9, the adhesive strength was largely lowered.

EXAMPLES 103 TO 109

The metal surface-treating agent used in Example 89 was stored in a constant temperature chamber of 37° C. for 2 months. According to the process of Example 79, "KINPARA 12", "WACROME", a pure gold plate and a pure copper plate were coated with the resultant metal surface-treating agent, and then air dried. The stainless steel bar was bonded to each of the adherends using "Bistite resin cement" (made by Tokuyama) to give adhesion test pieces (Example 103). Likewise, adhesion was carried out using the metal surface-treating agents which were used in Examples 82, 83, 84, 85, 86 and 87 and stored at 37° C. for 2 months, whereby adhesion test pieces (Examples 104 to 109) were obtained. One hour after the adhesion, each test piece was immersed in water of 37° C. for one hour, and 24 hours later, tensile adhesive strength was measured. The results are shown in Table 10.

TABLE 10

| | KINPARA 12 MPa | Pure gold plate MPa | WACROME MPa | Pure copper plate MPa |
|---|---|---|---|---|
| Example 103 | 28 (29) | 28 (28) | 36 (35) | 25 (27) |
| Example 104 | 25 (24) | 24 (26) | 33 (33) | 23 (24) |
| Example 105 | 23 (24) | 24 (24) | 33 (33) | 23 (24) |
| Example 106 | 27 (27) | 28 (28) | 34 (34) | 25 (26) |
| Example 107 | 25 (27) | 26 (27) | 32 (35) | 27 (27) |
| Example 108 | 27 (28) | 27 (27) | 33 (35) | 24 (26) |
| Example 109 | 28 (28) | 27 (28) | 33 (34) | 24 (25) |

( ) Initial adhesive strength

Also when the metal surface-treating agents after storage at 37° C. for 2 months were used (Examples 103 to 109), the adhesive strength to each metal was not greatly lowered, compared with the initial adhesive strength (the values in the parentheses in Table 10).

What is claimed is:

1. An unsaturated thiouracil derivative which has at least at one terminal thereof an organic group (I) having a radical polymerizable unsaturated bond, and has at the other terminal the following thiouracil residue (II)

$$\begin{array}{c} R^3 \quad O \\ \parallel \\ -OC-\!\!\!\!\!\!\!\!\!\!\!\!\!\!\!\!\!\!\!\!\!\!\!\diagup\!\!\!\diagdown\!\!\!\!\!\!\!\!\!\!\!\!\!\!\!\!\!N-R^1 \\ \parallel \quad \quad \diagdown\!\!\!\diagup \\ O \quad \quad N \\ \quad \quad \mid \\ \quad \quad R^2 \end{array} \quad S \qquad (II)$$

wherein $R^1$ and $R^2$ each is a hydrogen atom or an alkyl group, and at least one of $R^1$ and $R^2$ is a hydrogen atom, and $R^3$ is a hydrogen atom, an alkyl group or a phenyl group, and wherein the organic group (I) and the thiouracil residue (II) are separated by a bivalent spacer residue containing at least 2 carbon atoms.

2. An unsaturated thiouracil derivative according to claim 1 wherein the organic group (I) having a radical polymerizable unsaturated bond is represented by the following formula (I-1)

$$\begin{array}{c} R^5 \\ | \\ CH_2\!=\!C-Z- \end{array} \qquad (I\text{-}1)$$

wherein $R^5$ is a hydrogen atom or a methyl group, and Z is a —COO— group, a —CH$_2$O— group or a $$-\!\!\!\!\!\!\!\!\!\!\!\!\!\!\!\!\!\!\!\!\diagup\!\!\!\!\!\!\diagdown\!\!\!\!\!\!\!\!\!\!\!\!\!\!\!\!\!\!\!-CH_2O-$$

group, and the spacer residue is a bivalent organic group having 2 to 20 carbon atoms which may contain, in the chain skeleton, oxygen, or oxygen and silicon, besides carbon.

3. An unsaturated thiouracil derivative according to claim 1 or 2 wherein the spacer residue is a bivalent saturated hydrocarbon group having 2 to 12 carbon atoms, or any group selected from the following formulae (III-2), (III-3) and (III-4)

$$-\!(CH_2CH_2O\!)_n\!CH_2CH_2- \qquad (III\text{-}2)$$

$$\begin{array}{c} CH_3 \quad CH_3 \\ | \quad \quad | \\ -\!(CH_2)_o\!-\!(SiO)_q\!-\!Si\!-\!(CH_2)_p \\ | \quad \quad | \\ CH_3 \quad CH_3 \end{array} \qquad (III\text{-}3)$$

$$-\!(CH_2)_r\!-\!\!\!\!\!\!\!\!\!\!\!\!\!\!\!\!\!\!\!\diagup\!\!\!\!\!\!\diagdown\!\!\!\!\!\!\!\!\!\!\!\!\!\!-\!(CH_2)_s \qquad (III\text{-}4)$$

wherein n is an integer of 1 to 5, o and p each is an integer of 1 to 10, q is an integer of 1 to 5, and r and s each is an integer of 1 to 5.

4. An unsaturated thiouracil derivative represented by the following formula (1) or (2)

(1)

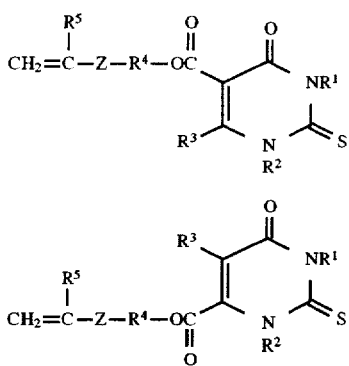

(2)

wherein $R^1$ and $R^2$ each are a hydrogen atom or an alkyl group, and at least one of $R^1$ and
$R^2$ is a hydrogen atom, and
$R^3$ i s a hydrogen atom, an alkyl group or a phenyl group,
$R^4$ is a bivalent saturated hydrocarbon group having 2 to 12 carbon atoms, or any group selected from the following formulae (III-2), (III-3) and (III-4)

 (III-2)

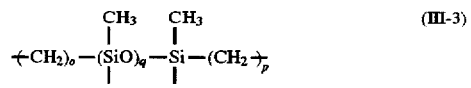 (III-3)

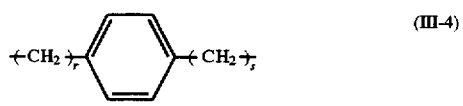 (III-4)

wherein n is an integer of 1 to 5, o and p each are an integer of 1 to 10, q is an integer of 1 to 5, and r and s each are an integer of 1 to 5,
Z is a —COO— group, a —CH$_2$O— group or a

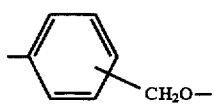

group, and
$R^5$ is a hydrogen atom or a methyl group.

5. A metal surface-treating agent comprising an unsaturated thiouracil derivative which
has at least at one terminal thereof an organic group (I) having a radical polymerizable unsaturated bond, and
has at the other terminal the following thiouracil residue (II)

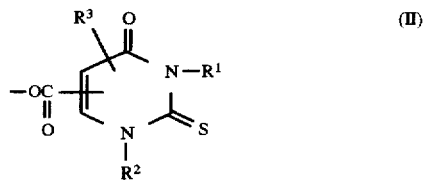 (II)

wherein
$R^1$ and $R^2$ each is a hydrogen atom or an alkyl group, and at least one of $R^1$ and
$R^2$ is a hydrogen atom, and $R^3$ is a hydrogen atom, an alkyl group or a phenyl group, and wherein the organic group (I) and the thiouracil residue (II) are separated by a bivalent spacer residue containing at least 2 carbon atoms.

6. A metal surface-treating agent according to claim 5 comprising an unsaturated thiouracil derivative in which the organic group (I) having a radical polymerizable unsaturated bond is represented by the following formula (I-1)

 (I-1)

wherein $R^5$ is a hydrogen atom or a methyl group, and Z is a —COO— group, a —CH$_2$O— group or a

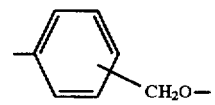

group, and
the spacer residue is a bivalent organic group having 2 to 20 carbon atoms which may contain, in the chain skeleton, oxygen, or oxygen and silicon, besides carbon.

7. A metal surface-treating agent according to claim 5 or 6 comprising an unsaturated thiouracil derivative in which the spacer residue is a bivalent saturated hydrocarbon group having 2 to 12 carbon atoms, or any group selected from the following formulae (III-2), (III-3) and (III-4)

 (III-2)

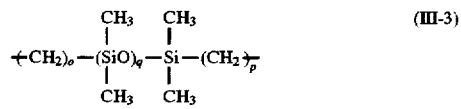 (III-3)

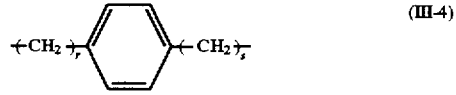 (III-4)

wherein n is an integer of 1 to 5, o and p each is an integer of 1 to 10, q is an integer of 1 to 5, and r and s each is an integer of 1 to 5.

8. A metal surface-treating agent comprising an unsaturated thiouracil derivative represented by the following formula (1) or (2)

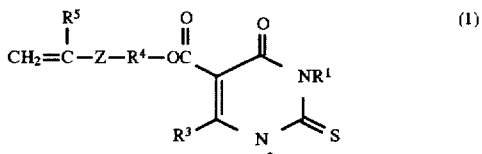 (1)

-continued

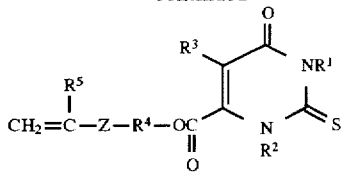
(2)

wherein

R$^1$ and R$^2$ each is a hydrogen atom or an alkyl group, and at least one of R$^1$ and
R$^2$ is a hydrogen atom, and
R$^3$ is a hydrogen atom, an alkyl group or a phenyl group,
R$^4$ is a bivalent saturated hydrocarbonic group having 2 to 12 carbon atoms, or any group selected from the following formulae (III-2), (111-3) and (III-4)

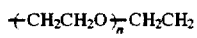 (III-2)

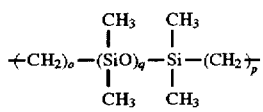 (III-3)

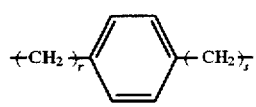 (III-4)

wherein n is an integer of 1 to 5, o and p each are an integer of 1 to 10, q is an integer of 1 to 5, and r and s each are an integer of 1 to 5, Z is a —COO— group, a —CH$_2$O— group or a

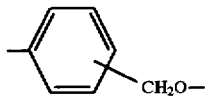

group, and
R$^5$ is a hydrogen atom or a methyl group.

9. A metal surface-treating agent according to any of claims 5, 6 or 8 further containing an organic solvent.

10. A metal surface-treating agent according to claim 9 wherein the concentration of the unsaturated thiouracil derivative is 0.001 to 20% by weight based on the total amount of the unsaturated thiouracil derivative and the organic solvent.

11. A metal surface-treating agent according to claim 9 wherein the organic solvent is acetone, toluene, methyl methacrylate or ethanol.

12. A metal surface-treating agent according to any of claims 5, 6 or 8 further containing an organic solvent and an acidic group-containing (meth)acrylate monomer.

13. A metal surface-treating agent according to claim 12 wherein, the compounding amount of the unsaturated thiouracil derivative is 0.001 to 20 weight parts, the compounding amount of the acidic group-containing (meth)acrylate monomer is 0.1 to 15 weight parts, and the rest is the organic solvent per 100 wt parts of total amount of the unsaturated thiouracil derivative, the acidic group-containing (meth)acrylate monomer and the organic solvent.

14. A metal surface-treating agent according to claim 12 wherein the acidic group-containing (meth)acrylate monomer is a (meth)acrylate monomer having a carboxyl group or a phosphoric acid group as the acidic group, and the organic solvent is acetone, toluene, methyl methacrylate or ethanol.

15. A metal surface-treating agent according to claim 7 further containing an organic solvent.

16. A metal surface-treating agent according to claim 10 wherein the organic solvent is acetone, toluene, methyl methacrylate or ethanol.

17. A metal surface-treating agent according to claim 7 further containing an organic solvent and an acidic group-containing (meth)acrylate monomer.

18. A metal surface-treating agent according to claim 13 wherein the acidic group-containing (meth)acrylate monomer is a (meth)acrylate monomer having a carboxyl group or a phosphoric acid group as the acidic group, and the organic solvent is acetone, toluene, methyl methacrylate or ethanol.

* * * * *

UNITED STATES PATENT AND TRADEMARK OFFICE
CERTIFICATE OF CORRECTION

PATENT NO. : 5,795,497
DATED : August 18, 1998
INVENTOR(S) : Kimura et al.

It is certified that error appears in the above-identified patent and that said Letters Patent is hereby corrected as shown below:

On the title page, insert item [30], "Foreign Application Priority Data"

Apr. 18, 1996 [JP] Japan ..............8-097174
Apr. 18, 1996 [JP] Japan..............8-097175
Dec. 26, 1996 [JP] Japan..............8-347849
Jan. 24, 1997 [JP] Japan..............9-011713

Signed and Sealed this

Twentieth Day of April, 1999

Attest:

Q. TODD DICKINSON

*Attesting Officer*      Acting Commissioner of Patents and Trademarks